US011531677B2

(12) United States Patent
Fonseca et al.

(10) Patent No.: US 11,531,677 B2
(45) Date of Patent: *Dec. 20, 2022

(54) SYSTEMS, METHODS, AND MEDIA FOR LABORATORY TESTING SERVICES

(71) Applicant: Laboratory Corporation of American Holdings, Burlington, NC (US)

(72) Inventors: Lidia L. Fonseca, Burlington, NC (US); Bill Leister, Charlotte, NC (US); Suresh Venkatraman, Irvine, CA (US); Michael Faisst, Cary, NC (US); George Harter, Burlington, NC (US); Kelly Curry, Burlington, NC (US); Paul Conlin, Burlington, NC (US); Roberto Verrengia, Burlington, NC (US); Louis Engel, Burlington, NC (US); Andrea Eastman, Burlington, NC (US); Piyush Jain, Burlington, NC (US)

(73) Assignee: Laboratory Corporation of America Holdings, Burlington, NC (US)

( * ) Notice: Subject to any disclaimer, the term of this patent is extended or adjusted under 35 U.S.C. 154(b) by 224 days.

This patent is subject to a terminal disclaimer.

(21) Appl. No.: 16/857,339

(22) Filed: Apr. 24, 2020

(65) Prior Publication Data

US 2020/0250187 A1     Aug. 6, 2020

Related U.S. Application Data

(63) Continuation of application No. 13/723,384, filed on Dec. 21, 2012, now Pat. No. 10,664,486.

(Continued)

(51) Int. Cl.
*G06F 16/2458* (2019.01)
*G16H 10/40* (2018.01)

(52) U.S. Cl.
CPC ......... *G06F 16/2471* (2019.01); *G16H 10/40* (2018.01); *Y02A 90/10* (2018.01)

(58) Field of Classification Search
CPC ...... G06F 16/2471; G16H 10/40; Y02A 90/10
See application file for complete search history.

(56) References Cited

U.S. PATENT DOCUMENTS

| 5,164,575 A | 11/1992 | Neeley et al. |
| 6,372,182 B1 | 4/2002 | Mauro et al. |

(Continued)

FOREIGN PATENT DOCUMENTS

| WO | 2013/096729 | 6/2013 |
| WO | 2013/096745 | 6/2013 |

OTHER PUBLICATIONS

U.S. Appl. No. 13/800,450, "Non-Final Office Action", dated Oct. 3, 2019, 29 pages.

(Continued)

*Primary Examiner* — Eliza A Lam
(74) *Attorney, Agent, or Firm* — Kilpatrick Townsend & Stockton LLP

(57) ABSTRACT

Systems, methods, and media for laboratory testing services are disclosed. A request for an electronic form can be received from an electronic device. A customized electronic form can be sent to the electronic device. The electronic form may be customized based at least in part on a healthcare provider associated with the request. At least one laboratory test may be requested to be ordered for at least one patient associated with the healthcare provider. At least one predefined rule may be applied to the requested order to verify that the order is valid. At least one laboratory can be selected to perform the ordered laboratory tests. Specimen collection information may be sent to a collection facility and can be based at least in part on rules or preferences of (Continued)

a lab selected to perform a laboratory test. Customized test reports can be provided to a healthcare provider.

20 Claims, 12 Drawing Sheets

Related U.S. Application Data

(60) Provisional application No. 61/584,936, filed on Jan. 10, 2012, provisional application No. 61/578,529, filed on Dec. 21, 2011.

(56) References Cited

U.S. PATENT DOCUMENTS

| | | | |
|---|---|---|---|
| 10,664,486 | B2 | 5/2020 | Fonesca et al. |
| 2002/0010625 | A1 | 1/2002 | Smith et al. |
| 2002/0147596 | A1 | 10/2002 | Vanderboom et al. |
| 2002/0161606 | A1 | 10/2002 | Bennett et al. |
| 2007/0016102 | A1 | 1/2007 | Askin |
| 2007/0294103 | A1 | 12/2007 | Ahmed et al. |
| 2008/0050278 | A1 | 2/2008 | Farina et al. |
| 2008/0195421 | A1 | 8/2008 | Ludwig et al. |
| 2009/0198520 | A1 | 8/2009 | Piovanetti-Perez |
| 2010/0036677 | A1 | 2/2010 | Daub, Jr. et al. |
| 2010/0169263 | A1 | 7/2010 | Korpman et al. |
| 2011/0029322 | A1 | 2/2011 | Hindo et al. |
| 2011/0153357 | A1 | 6/2011 | Zubiller et al. |
| 2011/0161106 | A1 | 6/2011 | Chapman et al. |
| 2011/0251960 | A1 | 10/2011 | Holla et al. |
| 2011/0265195 | A1 | 10/2011 | Chang et al. |
| 2012/0016685 | A1 | 1/2012 | Ryan et al. |
| 2013/0166315 | A1 | 6/2013 | Fonseca et al. |
| 2013/0166593 | A1 | 6/2013 | Fonseca et al. |
| 2013/0197943 | A1 | 8/2013 | Conlin et al. |

OTHER PUBLICATIONS

Patent Cooperation Treaty, International Search Report and Written Opinion, International Application No. PCT/US12/71197, dated Mar. 5, 2013.
Patent Cooperation Treaty, International Search Report and Written Opinion, International Application No. PCT/US12/71167, dated Mar. 5, 2013.
Patent Cooperation Teaty, Preliminary Report on Patentability, International Application No. PCT/US12/071167 dated May 14, 2015.
U.S. Appl. No. 13/800,450, Office Action dated Jan. 9, 2017.
U.S. Appl. No. 13/800,450, Office Action dated Jul. 13, 2016.
U.S. Appl. No. 13/800,450, Office Action dated Sep. 24, 2015.
U.S. Appl. No. 13/800,450, Office Action dated Mar. 4, 2015.
U.S. Appl. No. 13/800,450, Office Action dated May 5, 2014.
U.S. Appl. No. 13/800,450, Office Action dated Dec. 14, 2017.
U.S. Appl. No. 13/800,450, Office Action dated May 4, 2017.
Canadian Application No. 2,858,355, Office Action dated Aug. 6, 2015.
Canadian Application No. 2,858,355, Office Action dated Oct. 18, 2016.
Canadian Application No. 2,859,843, Office Action dated Dec. 10, 2015.
Canadian Application No. 2,859,843, Office Action dated Nov. 1, 2016.
Canadian Application No. 2,858,355, Office Action dated Aug. 28, 2017.
Austin Community College "Exercise 2: Venipuncture using vacuum collection system," Fall 2007.
U.S. Appl. No. 13/723,271, Non-Final Office Action, dated May 7, 2014, 33 pages.
U.S. Appl. No. 13/723,384, Corrected Notice of Allowability, dated Oct. 21, 2019, 3 pages.
U.S. Appl. No. 13/723,384, Final Office Action, dated Nov. 23, 2015, 20 pages.
U.S. Appl. No. 13/723,384, Final Office Action, dated Jun. 16, 2017, 25 pages.
U.S. Appl. No. 13/723,384, Final Office Action, dated Jun. 28, 2018, 28 pages.
U.S. Appl. No. 13/723,384, Non-Final Office Action, dated Oct. 6, 2014, 19 pages.
U.S. Appl. No. 13/723,384, Non-Final Office Action, dated Jan. 4, 2018, 22 pages.
U.S. Appl. No. 13/723,384, Non-Final Office Action, dated Oct. 11, 2016, 23 pages.
U.S. Appl. No. 13/723,384, Non-Final Office Action, dated May 31, 2019, 4 pages.
U.S. Appl. No. 13/723,384, Notice of Allowance, dated Aug. 28, 2019, 7 pages.
U.S. Appl. No. 13/723,384, Notice of Allowance, dated Jan. 24, 2020, 7 pages.
U.S. Appl. No. 13/800,450, Final Office Action, dated Mar. 31, 2020, 23 pages.
U.S. Appl. No. 13/800,450, Final Office Action, dated Jun. 13, 2019, 28 pages.
U.S. Appl. No. 13/800,450, Non-Final Office Action, dated Oct. 28, 2020, 22 pages.
U.S. Appl. No. 13/800,450, Non-Final Office Action, dated Sep. 17, 2018, 27 pages.
U.S. Appl. No. 13/800,450, Notice of Allowance, dated Mar. 8, 2021, 5 pages.
CA 2,858,355, Notice of Allowance, dated May 14, 2019, 1 page.
CA 2,858,355, Office Action, dated Jun. 26, 2018, 3 pages.
CA 2,859,843, Notice of Allowance, dated Oct. 3, 2017, 1 page.
PCT/US2012/071197, International Preliminary Report on Patentability, dated May 5, 2015, 7 pages.

SYSTEMS, METHODS, AND MEDIA FOR LABORATORY TESTING SERVICES

CROSS-REFERENCE TO RELATED APPLICATION

This application is a continuation of and claims priority to U.S. patent application Ser. No. 13/723,384, filed Dec. 21, 2012, entitled "Systems, Methods, and Media for Laboratory Testing Services,", which claims priority to U.S. Provisional Patent Application No. 61/584,936, filed Jan. 10, 2012, entitled "Systems, Methods, and Media for Laboratory Testing Services," and claims priority to U.S. Provisional Patent Application No. 61/578,529, filed Dec. 21, 2011, entitled "Systems, Methods, and Media for Laboratory Testing Services," the entirety of all of which are hereby incorporated by reference.

FIELD OF THE INVENTION

This disclosure relates generally to health care management and more particularly relates to the ordering, viewing, sharing, managing, analysis, delivery, and fulfillment of laboratory tests.

BACKGROUND

As the number of laboratory tests, health plans, and medical codes have increased, the complexity of managing the ordering, delivery, and fulfillment of laboratory tests has also increased. Systems and methods that reduce the complexity of ordering, delivery, and fulfillment laboratory tests are needed. Systems and methods that increase the efficiency of the delivery of health care services to a patient, by providing health care providers with better and more efficient means for obtaining, viewing, sharing, and/or analyzing clinical laboratory test results would be advantageous. Furthermore, systems and methods that increase the efficiency of the delivery of health care services to a patient, by providing health care providers with better and more efficient means for obtaining, viewing, sharing, and/or analyzing clinical laboratory test results on mobile devices, such as mobile computing devices, including, for example, mobile phones, mobile tablets, and the like, would be advantageous.

SUMMARY

Embodiments of the present invention provide systems, methods, and media for laboratory testing services. For example, one disclosed method comprises receiving medical information from an electronic device, the medical information comprising a plurality of identifiers; generating a customized response based at least in part on the received medical information, wherein generating the customized response comprises using at least one of the plurality of identifiers to query a data store comprising a plurality of laboratory tests, each of the plurality of laboratory tests beings associated with one or more identifiers; and sending the customized response to the electronic device.

These illustrative embodiments are mentioned not to limit or define the invention, but rather to provide examples to aid understanding thereof. Illustrative embodiments are discussed in the Detailed Description, which provides further description of the invention. Advantages offered by various embodiments of this invention may be further understood by examining this specification.

BRIEF DESCRIPTION OF THE FIGURES

The accompanying drawings, which are incorporated into and constitute a part of this specification, illustrate one or more examples of embodiments and, together with the description of example embodiments, serve to explain the principles and implementations of the embodiments.

DETAILED DESCRIPTION

Figure 1:
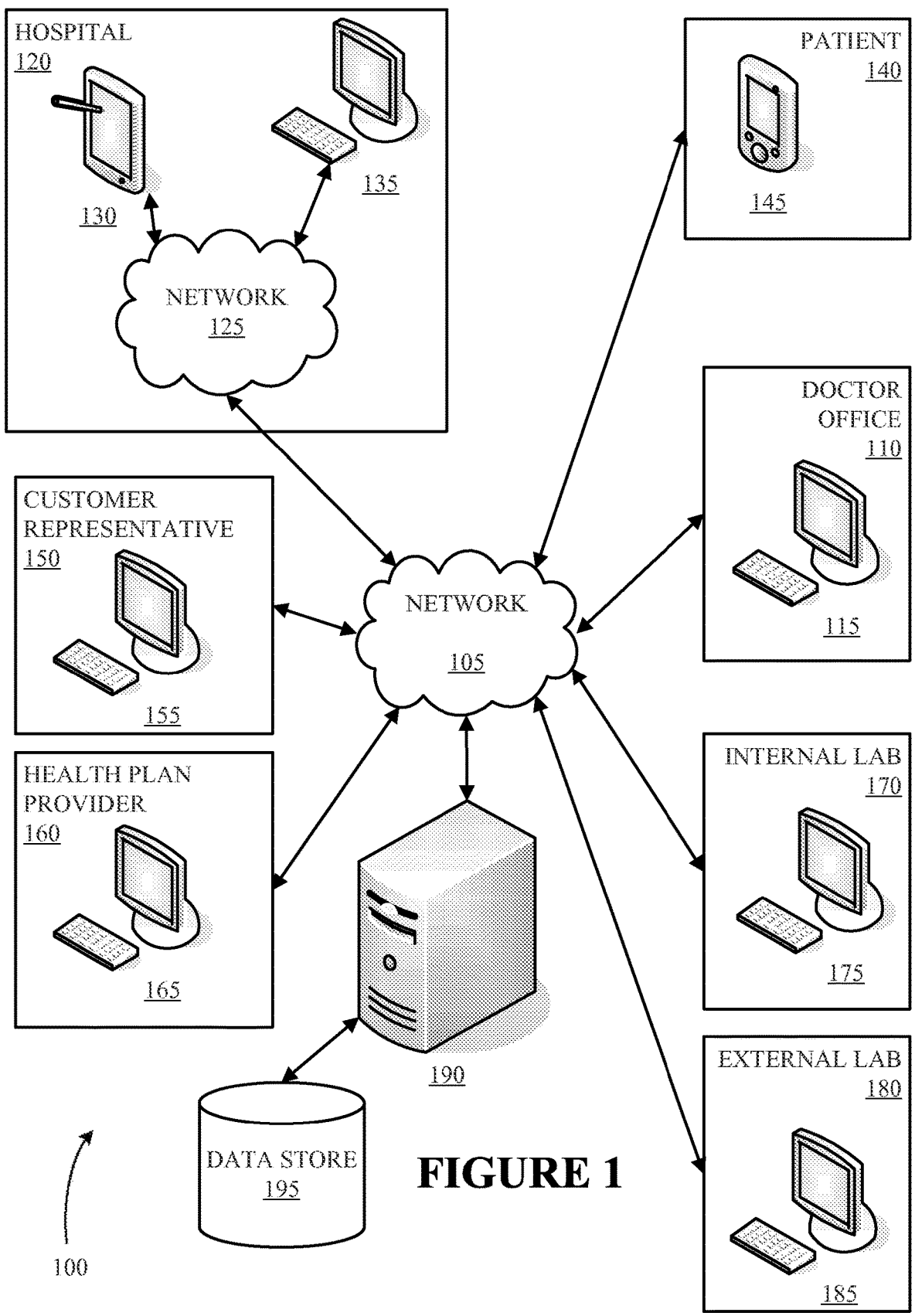
FIG. 1 is a system diagram depicting exemplary computing devices in an exemplary computing environment according to an embodiment.

Example embodiments are described herein in the context of systems and methods for the ordering, management, delivery, and/or fulfillment of clinical laboratory diagnostic tests. Those of ordinary skill in the art will realize that the following description is illustrative only and is not intended to be in any way limiting. Other embodiments, including embodiments relating to the ordering, management, viewing, analyzing, delivery, and/or fulfillment of other products, goods and/or services, will readily suggest themselves to such skilled persons having the benefit of this disclosure. Reference will now be made in detail to implementations of example embodiments as illustrated in the accompanying drawings. The same reference indicators will be used throughout the drawings and the following description to refer to the same or like items.

In the interest of clarity, not all of the routine features of the implementations described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another.

Illustrative Operation

In one embodiment, a healthcare provider uses an electronic device to access a website for managing the ordering, delivery, and/or fulfillment of laboratory tests. The healthcare provider can use the electronic device to order one or more laboratory tests for one or more patients through the website. For example, the healthcare provider can use the electronic device to access an electronic form for ordering laboratory tests through the website. In embodiments, the electronic form is customized. For example, the electronic form may be customized based at least in part on a healthcare provider. Thus, in one embodiment, the electronic form may comprise one or more predefined test groups corresponding to a healthcare provider. Each predefined test group may be associated with one or more laboratory tests. In this embodiment, the customized electronic form may be configured such that each laboratory test in a predefined test group is selected when that when the predefined test group is selected. In one embodiments, the customized electronic form may comprise frequently ordered laboratory tests for a particular healthcare provider. As another example, the customized electronic form may contain frequently ordered laboratory tests across a plurality of healthcare providers. The customized electronic form may include information for laboratory tests for particular diseases. For example, if a healthcare provider uses an electronic device to select a particular disease, then the customized form may include frequently ordered laboratory tests for the selected disease.

When an order for one or more laboratory tests is received, one or more criteria may be used to determine if the order can be placed and/or fulfilled. For example, if an order for a laboratory test for a patient is received, then information associated with an account of the patent may be accessed to determine whether there is an outstanding balance for the account. If there is an outstanding balance, a payment notice may be generated. As another example, a server receiving a request for an order of one or more laboratory tests may determine one or more laboratories to complete at least a portion of the order based on geographic preferences, cost, delivery requirements and/or other factors.

The healthcare provider may receive fulfillment instructions through the website. For example, if a healthcare provider uses an electronic device to submit an order for one or more laboratory tests to a server, then the electronic device may receive fulfillment instructions from the server. The fulfillment instructions can include instructions for handling and/or delivering a specimen to be collected for the order. For example, fulfillment instructions may include an amount of a sample to collect, a tube size to use, the color of a top to be used for a test tube, an order for collecting two or more samples, or other fulfillment instructions.

The healthcare provider can receive test results through the website, email, or other electronic notifications. For example, a healthcare provider can receive tests results in response to submitting a request through the website. A healthcare provider may receive test results electronically at predetermined times, such as a periodic basis, when each test in an order is complete, and/or when all tests in an order are complete. In one embodiment, a healthcare provider receives a customized test results report. The customized test results report can include information in addition to the actual results of the one or more ordered laboratory tests. For example, a customized the results report can include historical laboratory test results for a patient. Numerous other embodiments are disclosed herein and variations are within the scope of this disclosure.

This illustrative example is given to introduce the reader to the general subject matter discussed herein. The invention is not limited to this example. The following sections describe various additional non-limiting embodiments and examples of devices, systems, and methods for lab testing management.

Illustrative System

FIG. 1 is a system 100 diagram depicting exemplary computing devices in an exemplary computing environment according to an embodiment. The system 100 shown in FIG. 1 includes a network 105 in communication with various devices associated with doctor offices 110, hospitals 120, patients 140, customer representatives 150, health plan providers 160, internal labs 170, and external labs 180. The various devices that network 105 can be in communication with include, but is not limited to, a desktop computer (i.e. 155), a tablet computer (i.e. 130), or a mobile phone (i.e. 145). The network 105 in FIG. 1 is also in communication with a server 190 and the server 190 is in communication with a data store 195. The network 105 may be in communication with other networks such as, for example, network 125 which associated with the hospital 120. In embodiments, the various devices can send and receive messages with other devices associated with network 105. Thus, a desktop computer 115 in the doctor's office 110 may be able to communicate with server 190 through the network 105. As another example, a desktop computer 175 associated with an internal lab 170 may be able to receive information from data store 195 or store information to data store 195, or both, through the network 105 and the server 190.

In embodiments, various devices including, but not limited to, desktop computer 115, tablet computer 130, and mobile phone 145, may be any device capable of communicating with a network, such as network 105, and capable of sending and receiving information to and from another device. For example, in FIG. 1, one device may be a tablet computer 130. The tablet computer 130 may include a touch-sensitive display and be able to communicate with network 105 through network 125 by using a wireless network interface card. Another device shown in FIG. 1 is a desktop computer 115. The desktop computer 115 may be in communication with a display and be able to connect to network 105 through a wired network connection. The desktop computer 115 may be in communication with any number of input devices such as a keyboard or a mouse. In FIG. 1, a mobile phone 145 is another device that is associated with a patient 140. The mobile phone 145 may be able to communicate with the network 105 over a wireless communications means such as TDMA, CDMA, GSM, or WiFi. In various embodiments, one or more mobile phones, tablets, desktop computers, or other suitable computing devices may be associated with one or more healthcare providers, patients, customer representatives, health plan providers, internal labs, external labs, or other users.

In embodiments, network 105 shown in FIG. 1 facilitates communications between the various devices (i.e. 145, 155, 175, 185, etc.) and server 190. The network 105 may be any suitable number or type of networks or links, including, but not limited to, a dial-in network, a local area network (LAN), wide area network (WAN), public switched telephone network (PSTN), the Internet, an intranet or any combination of wired and/or wireless communication links. In one embodiment, the network 105 may be a single network. In other embodiments, the network 105 may comprise two or more networks. For example, the various devices may be connected to a first network, such as network 125, and the server 190 may be connected to a second network, such as network 105, and the first and the second network may be connected. Numerous other network configurations would be obvious to a person of ordinary skill in the art.

In embodiments, network 125 shown in FIG. 1 facilitates communications between the various devices (i.e. 130, 135, 145 etc.) and server 190. The network 125 may be any suitable number or type of networks or links, including, but not limited to, a dial-in network, a local area network (LAN), wide area network (WAN), public switched telephone network (PSTN), the Internet, an intranet or any combination of wired and/or wireless communication links. In one embodiment, the network 105 may be a single network. In other embodiments, the network 105 may comprise two or more networks. For example, various devices may be connected to a first network, such as network 125, and the server 190 may be connected to a second network, such as network 105, and the first and the second network may be connected.

In FIG. 1, network 125 is associated with hospital 120. In embodiments, any number of entities may be associated with one or more networks. For example, a network associated with customer representative 150 may be in communication with network 105. Likewise, a network associated with an external lab 180 may be associated with network 105. Numerous other networks associated with entities—such as a doctor's office 110, a health plan provider 160, patient 140, or internal lab 170—and connected with network 105 may be present in various embodiments. Other network configurations would be obvious to a person of ordinary skill in the art.

In embodiments, communication between devices, networks, or entities, or some combination thereof, may be facilitated by the Internet. For example, network 105 may be in communication with network 125 through the Internet. In embodiments, communication may be secure. For example, a hypertext transfer protocol secure (HTTPS) may be used to provide encrypted communication between various devices, networks, or entities, or some combination thereof. In another embodiment, a virtual private connection (VPN) may be used to provide communication. For example, a gateway associated with network 125 can be in communication with a gateway associated with network 105 through a VPN connection. In one embodiment, a VPN connection may contain a single tunnel connection. To at least provide redundancy, however, a VPN connection may comprise two or more tunnel connections. Thus, if one tunnel connection in the VPN connection fails, communication may still be successful through the other tunnel connection.

The server 190 shown in FIG. 1 may be any device capable of communicating with a network, such as network 105, and capable of sending and receiving information to and from another device. For example, in the embodiment shown in FIG. 1, the server 190 may receive a request from various devices such as tablet computer 130, mobile phone 145, desktop computer 155, or other devices. In this embodiment, the server 190 may respond to the request by sending information back to the requesting device through the network 105. Thus, if server 190 receives a request from desktop computer 115 associated with doctor office 110 through network 105, then the server 190 may process the request including performing any necessary communication with any other device and respond to the request by sending a response back to the desktop computer 115 through the network 105. In an embodiment, the server 190 can communicate with a gateway associated with the server and network 105. The server 190 may be in communication with one or more data stores, such as data store 195.

In embodiments, server 190 may be in communication with one or more additional devices, such as additional servers. In some embodiments, server 190 may communicate with one or more additional devices to process a request received from another device. For example, the server 190 in FIG. 1 may be in communication with a plurality of additional servers, at least one of which may be used to process at least a portion of a request received from another device, such as tablet computer 130, mobile phone 145, or desktop computer 175. In other embodiments, the server 190 may send a request to one or more devices and process any response received from the device or devices. For example, server 190 may send a request to desktop computer 135 associated with hospital 120. In this embodiment, the server 190 may receive a response from the desktop computer 135 and process the response. For example, the server 190 may store information related to the response in data store 195.

The system 100 shown in FIG. 1, includes a data store 195. The data store 195 can include numerous separate data stores, data tables, databases, or other data storage mechanisms and media for storing data relating to particular aspects of one or more of the embodiments disclosed herein.

Figure 2:
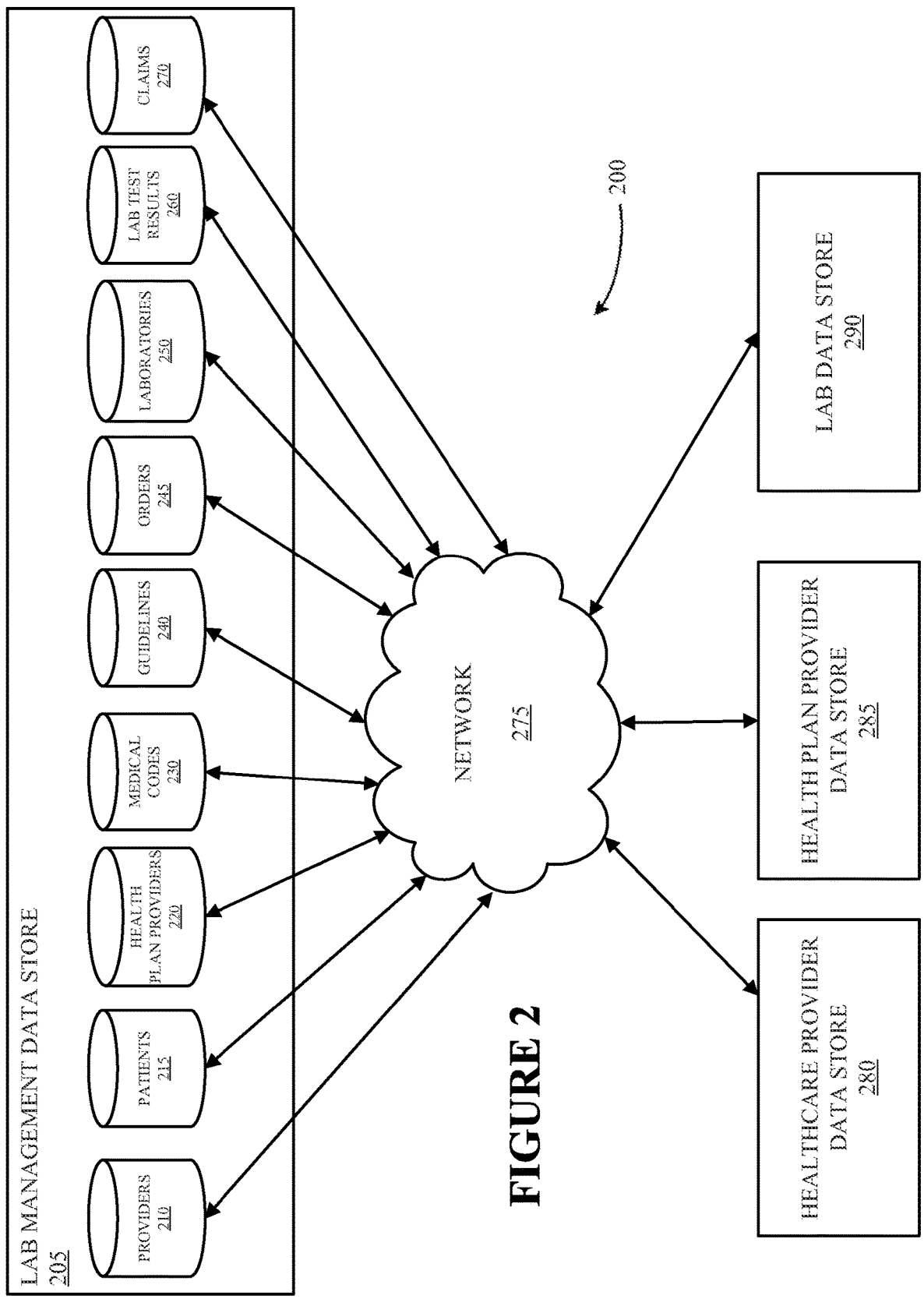
FIG. 2 is a system diagram illustrating various data stores that can store information according to an embodiment.

FIG. 2 provides a system 200 diagram illustrating various data stores 205, 280-290 that can store information according to an embodiment. In the system 200 shown in FIG. 2, a lab management data store 205, a healthcare provider data store 280, a health plan provider data store 285, and a lab data store 290 are in communication with each other through network 275. Information stored in a data store may be accessed by one or more other data stores. For example, information stored in the health plan provider data store 285 may be accessed by the lab management data store 205. In embodiments, information stored in the lab management data store 205 may be accessed by the health plan provider data store 285. Information may be sent to or saved by, or both, one or more data stores from another data store. For example, information regarding a lab testing order may be sent by the healthcare provider data store 280 through network 275 the lab management data store 205. In this embodiment, the lab management data store 205 may store lab testing order data to the orders database 245. In another embodiment, information regarding the results of a lab test may be sent from lab management data store 205 to healthcare provider data store 280. In various embodiments, information stored in data stores 205, 280, 285, and 290 may contain information stored in data store 195 shown in FIG. 1 according to various embodiments.

In embodiments, network 275 shown in FIG. 2 facilitates communications between the various data stores 205, 280, 285, and 290. The network 105 may be any suitable number or type of networks or links, including, but not limited to, a dial-in network, a local area network (LAN), wide area network (WAN), public switched telephone network (PSTN), the Internet, an intranet or any combination of wired and/or wireless communication links. In one embodiment, the network 105 may be a single network. In other embodiments, the network 105 may comprise two or more networks. For example, the various devices may be connected to a first network, such as network 125, and the server 190 may be connected to a second network, such as network 105, and the first and the second network may be connected. Numerous other network configurations would be obvious to a person of ordinary skill in the art.

In the embodiment shown in FIG. 2, the lab management data store 205 comprises information related to various aspects of a lab management system. The lab management data store 205 in FIG. 2 comprises information related to healthcare providers 210. For example, information related to health care providers 210 can include names, addresses, phone numbers, personnel, usernames, passwords, other security information, access levels, and other information associated with one or more providers. The lab management data store 205 in FIG. 2 contains information related to patients 215. Information related to patients 215 may include patient names, addresses, telephone numbers, providers to which the patients are associated, medical history, medications, relatives, health care provider plans, account balances, access information, or other information related to one or more patients.

In FIG. 2, the lab management data store 205 includes information related to health plan providers 220. For example, information related to health plan providers can include insurance companies, various insurance plans, payment information for lab tests, information related to one or more patients, deductible information, testing authorization data, or other information associated with one or more health plan providers. The lab management data store 205 in FIG. 2 comprises information related to medical codes 230. Such information may include medical classifications for diseases, signs, symptoms, potential causes of injury, potential causes of one or more diseases, testing procedures, laboratory tests, other coding information, or a combination thereof. For example, in one embodiment, information related to medical codes 230 can include data from the International Statistical Classification of Diseases and Related Health Problems (ICD) such as the ICD-9 medical classification list or the ICD-10 medical classification list. In another embodiment, information related to medical codes 230 may include data such as the American Medical Association's (AMA) CPT data code files that provide at least a list of CPT procedural codes.

The lab management data store 205 in FIG. 2 contains information related to medical guidelines 240. Information related to medical guidelines 240 can include evidence based guidelines for one or more diseases, illnesses, medical tests, etc. In an embodiment, information related to medical guidelines 240 includes information that may be used to offer suggestions regarding tests or procedures that are typically followed for a particular illness, system or set of symptoms, or other evidence-based information. In one embodiment, a set of questions related to one or more illnesses or one or more symptoms made be stored in data base 240. The lab management data store 205 in FIG. 2 includes information related to orders 245. For example, information related to orders 245 can include information related to health care providers that have placed an order, information related to patients for which an order has been placed, information related to the tests that have been performed, billing information, payment information, accounts receivable information, order status, tracking information, one or more laboratories associated with orders, test results, or a combination thereof.

The lab management data store 205 in FIG. 2 comprises information related to laboratories 250. For example, a laboratories database 250 may contain information such as location, costs for various tests, turnaround time, type of tests performed, current capacity levels, historical information related to tests that have been performed by one or more laboratories, current information regarding one or more orders such as order statuses, tracking information, addresses, personnel, contacts, profit margins such as profit margins for one or more tests, usernames, passwords, other identification, or other laboratory information. In embodiments, the laboratories database 250 may contain information to distinguish internal laboratories from external laboratories. Internal laboratories can include laboratories owned by or affiliated with one or more organizations operating a laboratory management system. For example, if an organization is operating the laboratory management system described herein and the organization owns a laboratory, in one embodiment, the laboratory can be considered an internal laboratory. Examples of external laboratories can include laboratories not owned or operated by an organization operating the laboratory management system. For example, in one embodiment, an organization may own several laboratories, but none of the internal laboratories perform a particular test that has been ordered. In this embodiment, the laboratories database 250 may contain information for an external laboratory that has the capability to perform the test. Numerous other embodiments or additional information that may be stored in the laboratories database 250 will be obvious to one of skill in the art.

The lab management data store 205 in FIG. 2 contains information related to lab test results 260. Information related to lab test results 260 can include information such as the actual results of the test, suggested follow-up tests, historical information based on past test results, diagnostic information, information related to medical guidelines or thresholds for one or more tests, and other information related to test results. The lab management data store 205 in FIG. 2 includes information related to claims 270. For example, information related to claims can include the payment status for claims, tracking information, whether the claim has been submitted to a health plan provider, eligibility verification information, benefits determination information, whether a claim requires editing, whether the claim needs or has been adjusted, or other information related to one or more claims.

In various embodiments, information stored in data stores 205, 280, 285, and 290 may contain information stored in data store 195 shown in FIG. 1 according to various embodiments. It should be understood that there can be many other aspects that may need to be stored in data stores 205, 280, 285, or 290, or some combination thereof. In various embodiments, information shown in data store 205 may be stored in any number of data stores including, but not limited to, data store 280, 285, or 290. In some embodiments, data store 205 may access or store information, or both, in one or more data stores, such as data store 280, 285, or 290. For example, in one embodiment, data store 290 may contain lab test results 260. In this embodiment, data store 205 may be able to access information or store information related to lab test results 260 by accessing data store 290 through network 275. One or more data stores may be associated with any number of entities. For example, data store 280 may be associated with a healthcare provider such as a hospital or a doctor's office. In one embodiment, data store 280 may be associated with a hospital and one or more satellite branches such as other facilities located in surrounding communities. In other embodiments, data store 280 may be associated with multiple hospitals or other facilities owned, affiliated with, or related to one another. Data store 285 may be associated with a health plan provider such as an insurance company. Data store 290 may be associated with one or more labs such as an internal lab or an external lab. It should be understood that information may be stored in any appropriate mechanisms or in additional mechanisms in one or more of data stores 205, 280, 285, or 290.

Referring back to FIG. 1, data store 195 is operable, through logic associated therewith, to receive instructions from various devices—such as server 190, other data stores, networks 105 or 125, other devices (i.e. 130, 145, 175, etc.), or a combination thereof—and obtain, update, or otherwise process data in response thereto. As one example, a doctor's office 110 may submit an order for a lab test for a patient using desktop computer 115 to the server 190 through network 105. In this case, the server 190 may process the order at least by querying the data store 195 to verify the identity of the doctor's office and, if the doctor's office is authorized, process the order. It should be understood that there can be many other aspects that may need to be stored in the data store 195, such as page image information or access rights information, which can be stored in any appropriate mechanisms or in additional mechanisms in the data store 195.

In FIG. 1 numerous entities, such as hospital 120 and internal lab 170, are shown. In various embodiments, any number of entities may be associated with network 105 or can send information to server 190 or receive information from server 190, or some combination thereof. In the embodiment shown in FIG. 1, healthcare providers, including hospital 120 and doctor office 110, as well as patient 140 are in communication with network 105. A healthcare provider can be any personnel or facility that provides health care services to one or more patients. A patient can be anyone who receives treatment from a healthcare provider. In FIG. 1, a customer representative 150 is in communication with network 105. In embodiments, a customer representative 150 may be one or more companies or individuals that provide support to patients 140 or entities (i.e. hospital 120, internal lab 170, health plan provider 160, etc.), or both. For example, a patient 140 may call a customer representative 150 to verify the status or results of a lab test that was ordered for the patient. Numerous entities may be in communication with network 105, additional networks, other entities, or additional devices according to various embodiments of the present invention.

The environment in an embodiment is a distributed computing environment utilizing several computer systems and components that are interconnected via communication links, using one or more computer networks or direct connections. However, it will be appreciated by those of ordinary skill in the art that such a system could operate equally well in a system having fewer or a greater number of components than are illustrated in FIG. 1. Thus, the depiction of the system 100 in FIG. 1 should be taken as being illustrative in nature, and not limiting to the scope of the disclosure.

Illustrative Operation and Method

Figure 3:
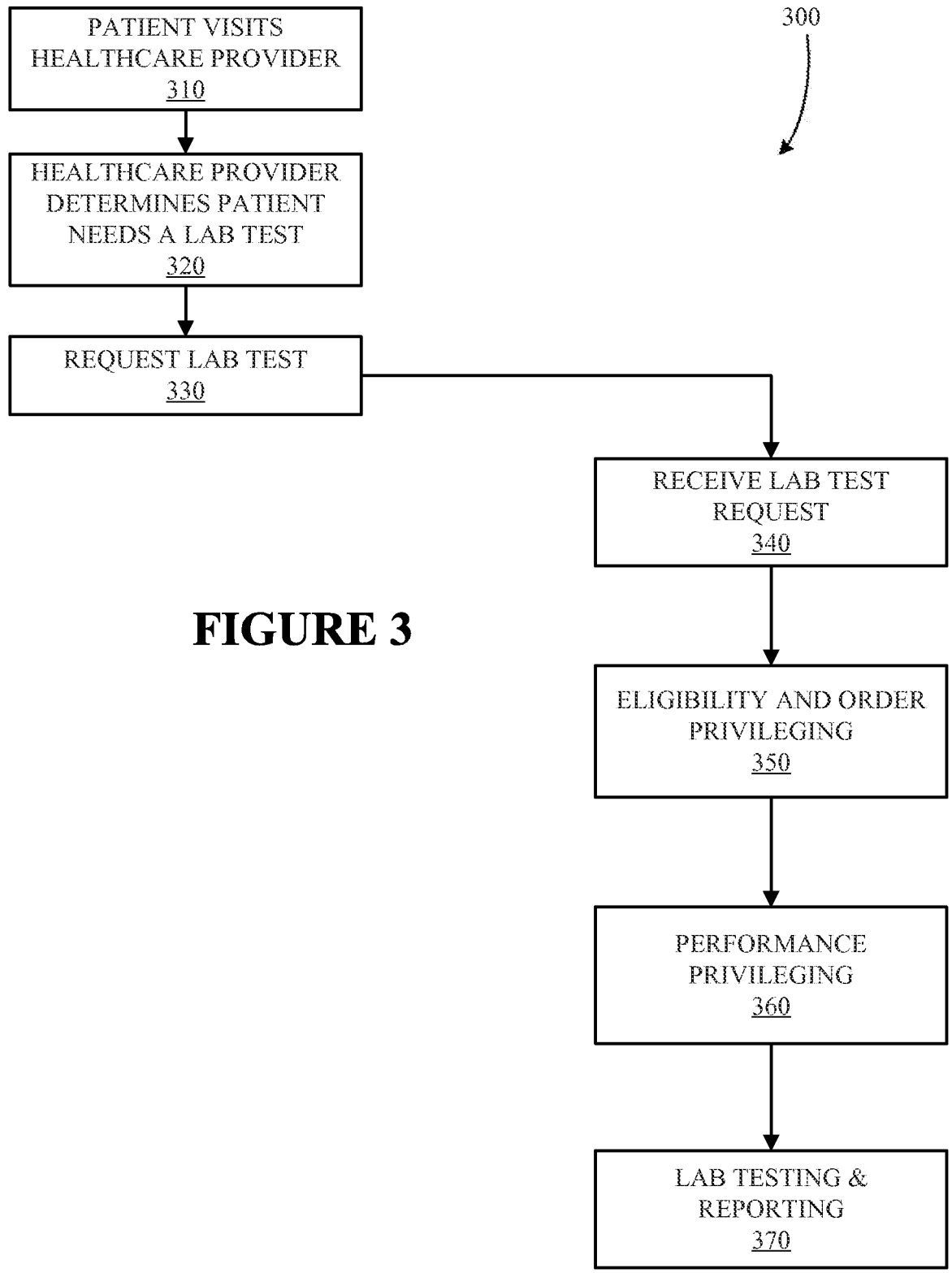
FIG. 3 is a flow chart illustrating an operation of and systems and methods for a laboratory benefit management system according to an embodiment.

FIG. 3 is flow chart illustrating an operation of an example systems and methods for a laboratory benefit management system according to an embodiment. The method shown in FIG. 3 will be described with respect to the environment shown in FIG. 1.

The method 300 shown in FIG. 3 begins when a patient visits a healthcare provider 310. For example, referring to FIG. 1, the patient 140 may visit a physician at a doctor's office 110. Once the patient visits the healthcare provider 310, the method proceeds to block 320. In block 320, the healthcare provider determines that a patient needs at least one lab test. For example, referring to FIG. 1, the physician at the doctor's office 110 may determine that the patient 140 needs a lipoprotein analysis.

Once the healthcare provider determines that the patient needs at least one lab test 320, at least one lab test may be requested 330. A lab test may be requested by any number of persons. For example, referring to FIG. 1, personnel in the doctor's office may request the lab test 120. In embodiments, the physician requesting the lab test, another physician, a nurse, an administrative assistant, other office personnel, or other persons associated with the healthcare provider may request the lab test. A lab test may be requested in any number of ways. For example, a lab request may be called in to a lab management organization or faxed to the lab management organization. In one embodiment, personnel associated with the healthcare provider may use one or more devices to electronically submit a lab request to a lab management organization. For example, referring to FIG. 1, a nurse associated with doctor's office 110 may use desktop computer 115 to send an email to a lab management organization associated with server 190 and the email may contain information related to a lab test request.

In another embodiment, a person submitting a lab test request may visit a website designed to receive lab test requests. For example, referring again to FIG. 1, a doctor may visit a website associated with a lab management organization using desktop computer 110 by sending a request to server 190 through network 105. In response to the request, the server 190 may send a response to the desktop computer 115 through network 105. For example, the server 190 can send a response to the desktop computer 115 with an electronic form, such as an HTML form and/or AJAX-based form, that a user of the desktop computer 115 can fill out to complete at least a portion of the order. The form may provide healthcare provider-specific information. For example, the form may provide a preselected grouping of commonly ordered tests for a particular physician. In this embodiment, the person ordering the lab test authorized by the physician can select a test name associated with the preselected grouping of laboratory tests to order each of the tests in the preselected grouping for one or more patients.

In embodiments, a response to a request can include a customized response. For example, in one embodiment medical information is received from an electronic device and the medical information comprises a plurality of identifiers. In this embodiment, a customized response can be generated based at least in part on the received medical information. For example, a customized response may be generated by using at least one of the plurality of identifiers to query a data store comprising a plurality of laboratory tests. Each of the plurality of laboratory tests can be associated with one or more identifiers. Thus, the data store can comprises a plurality of laboratory tests and one or more identifiers associated with each of the plurality of laboratory tests. For example, a customized response may include a laboratory test that has an identifier corresponding to an identifier received in a request. In another embodiment, generating a customized response can include determining a predefined test group for the healthcare provider. The predefined test group may correspond to a predefined plurality of laboratory tests. Generating a customized response in an embodiment can include generating a customized electronic form for ordering laboratory test. The customized electronic form may comprise a predefined test group. The customized electronic form can be configured such that each laboratory test in the predefined plurality of laboratory tests are selected when the predefined test group is selected. A customized electronic form may include a subset of a plurality of frequently ordered laboratory tests. In one embodiment, generating a customized form includes determining a plurality of frequently ordered laboratory tests for the healthcare provider. Generating a customized form may include determining a plurality of frequently ordered laboratory tests across a plurality of healthcare providers comprising the healthcare provider type. Numerous other embodiments are disclosed herein and variations are within the scope of this disclosure.

The website may contain one or more security measures, such as requiring a username and password or a digital certificate, to verify the authenticity of the doctor submitting the lab request. For example, the server 190 may access data store 195 to determine whether information received from the desktop computer 115 associated with the doctor's office 110 successfully authenticates a user of the desktop computer 115. In this embodiment, once the authenticity of the doctor has been verified, the website may contain one or more forms that the doctor can fill out to request a lab test for the patient. In another embodiment, a lab test request may be received by server 190 from various devices through an application programming interface (API) call. In various embodiments, one or more applications, such as a desktop application or a Windows®-based application, associated with the healthcare provider may be executed that facilitates submitting one or more lab test requests to a lab management organization. For example, tablet computer 130 associated with hospital 120 may contain an application that can be executed by a user to submit a lab test request to a lab management organization. The application may be able to communicate with other devices, such as server 190, through network 105 and network 125.

When a device, such as tablet computer 130 or desktop computer 115, requests a lab test 330, another device may receive the lab test request 340. For example, if an administrator at hospital 120 uses tablet computer 130 to request a lab test 330 for a patient, then server 190 may receive the lab test request 340 through network 105 and network 125. In embodiments, the device receiving the lab test request may process the request. For example, if server 190 receives a lab test request from desktop computer 115, then server 190 may process the request. In embodiments, a device sending a lab test request and a device receiving a lab test request may send and receive information back and forth to process the request. For example, if a lab test request is in some way incomplete then the device receiving the lab test request may send information to the requesting device asking for additional information and the requesting device may send the additional information to the device that received the lab test request.

In one embodiment, when a lab test request is received 340, the lab test request is processed through an eligibility and order privileging component 350. In the eligibility and order privileging component 350, a lab test request may be verified for completeness. For example, when a lab test request for one or more lab tests is received, at least a portion of the lab test request may be analyzed by one or more rules—such as healthcare provider rules, insurance provider rules, and/or application-specific rules—to determine whether the order should be processed. Information from the lab test request may be used to verify that the requestor has access or appropriate privileges to submit a lab test request. Information regarding a patient may be analyzed to determine whether the patient is eligible to receive the requested lab test. For example, information related to a patient's healthcare provider or healthcare plan may be analyzed to determine whether the patient is authorized to receive the requested lab test or tests. In some embodiments where someone other than the physician treating the patient submits a lab test request for the patient, the physician may be notified of the request. In one embodiment, the physician must approve the lab test request before the lab test or tests associated with the request are ordered.

In an embodiment, a lab test request 340 may be received that contains one or more tests for one or more patients that needs to be ordered. In another embodiment, a lab test request 340 may contain present or historical, or both, medical information related to one or more patients and this information may be used to verify a patient's eligibility for a particular test. Information received in a lab test request may be collected or verified in response to receiving a lab test request. For example, information contained in a lab test request may be verified against one or more medical classification lists such as ICD-9, ICD-10, or CPT data. Numerous other embodiments are disclosed herein and variations are within the scope of this disclosure.

Any lab test or tests that are ordered may be processed through a performance privileging module 360. In some embodiments, the performance privileging module can determine one or more laboratories to perform at least a portion of a test for an order. Such a determination may be based on any number of factors. For example, a determination may be based on a timeframe for completing at least a portion of the order. In this embodiment, a laboratory that has the capacity to provide lab results for the portion of the order may be selected. A determination may be based at least in part on the profitability for at least a portion of an order. For example, if an order specifies a particular lab test and ten laboratories are available to complete the lab test, then the lab with the overall lowest cost for performing the lab test may be chosen. A determination can be based on other factors such as location of the laboratory, whether the laboratory is an in-network or out-of-network laboratory, whether the laboratory is owned or operated by the lab management organization, other factors, or a combination thereof.

Information regarding the collection of one or more samples of an ordered lab test may be sent to a healthcare provider. For example, if a nurse submits an order for two laboratory tests to server 190 using desktop computer 115, then server 190 may send sample collection information to desktop computer 115. Sample collection information can include information such as the size of one or more tubes to be used, handling instructions, filling instructions, a minimum sample amount, a maximum sample amount, a sample tube top color, other procedure or collection information, or a combination thereof. Numerous variations are disclosed herein and others variations are within the scope of this disclosure.

One or more of the lab tests may be processed through a lab testing and reporting module 370. The lab testing and reporting module 370 may track the status of a lab test. For example, if an external laboratory is selected to perform a lab test, then the lab testing module may track the status of the lab test. The status of the lab test may include information such as whether a sample related to the test has been collected, the historical location of the sample, a current location of the sample, whether the lab test has been started, an expected completion date for the lab test, whether the results of a lab test are available, whether the results of a lab test have been received, or other status information. In embodiments, status information may be exchanged between various devices. For example, referring to FIG. 1, an internal lab 170 may send status information to server 190 through network 105 which is stored in data store 195. In one embodiment, status information may be sent from server 190 to an external lab 180 through network 105.

Various entities may be able to access at least some information regarding a lab test. For example, a physician or other personnel in doctor's office 110 may be able to view the status of one or more lab tests. A physician may be able to view the results of one or more lab tests. In one embodiment, a healthcare provider can customize the presentation of results of one or more lab tests. For example, one healthcare provider may customize test results so that only raw data related to the lab test is sent in the test results. Another healthcare provider may customize test results so that raw data as well as graphical indications, such as a bar chart or a pie chart, is shown in a test results report. In another embodiment, the healthcare provider can customize the test results report to include historical medical information related to one or more patients. In yet another embodiment, the healthcare provider can customize test results reports to include one or more recommendations based at least in part on the test results. In some embodiments, one or more persons associated with a healthcare provider can customize test results reports. For example, a healthcare provider may have a customized test results report template and a doctor employed by the healthcare provider may have another customized test results report template. Thus, various entities or people associated with various entities, or both, may be able to customize test reports. In some embodiments, a patient may be able to customize test results reports. Variations are within the scope of this disclosure and will be apparent to one of skill in the art.

This illustrative example is given to introduce the reader to the general subject matter discussed herein. The invention is not limited to this example. The following sections describe various additional non-limiting embodiments and examples of devices, systems, and methods for lab testing management.

Eligibility and Order Privileging Component

Figure 4:
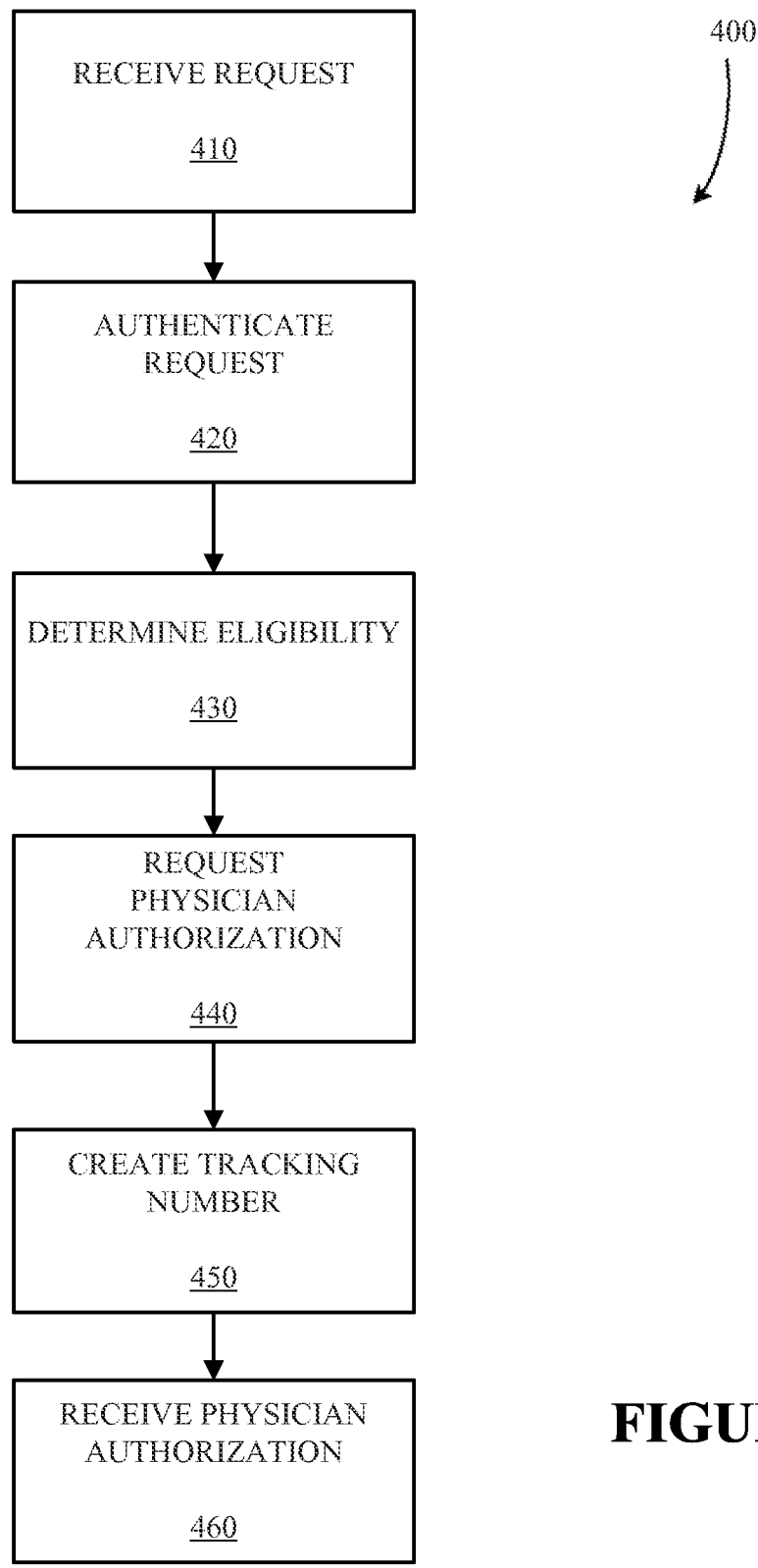
FIG. 4 is a flow chart illustrating a method for an eligibility and order privileging component of a laboratory benefit management system according to an embodiment.

FIG. 4 is a flow chart illustrating a method 400 for an eligibility and order privileging component of a laboratory benefit management system according to an embodiment. For example, one or more steps described with respect to method 400 may be performed in the eligibility and order privileging component 350 shown in FIG. 3. The description of method 400 will be made with respect to FIG. 1, which illustrates an example environment 100 for implementing aspects in accordance with various embodiments.

The method 400 begins in block 410 when a request is received. A request may be received by any number of electronic devices in communication with a sending device. A request may be associated with one or more healthcare providers. For example, in FIG. 1 the server 190 may receive a request from tablet computer 130 associated with hospital 120 through network 105 and network 125. In another embodiment, the server 190 may receive a request from desktop computer 115 associated with doctor's office 110 through network 105. In some embodiments, the server 190 may ask for information from one or more electronic devices and receive a request back from the one or more electronic devices. For example, server 190 may communicate with desktop computer 135 associated with hospital 120 to determine whether there are any order requests that the hospital needs to place. In this embodiment, if the hospital 120 has one or more outstanding order requests, then the desktop computer 135 associated with the hospital 120 may send one or more requests to server 190.

A request may be received by one or more electronic devices in any number of ways. A request may be received over various communication protocols. For example, a request may be received over hypertext transfer protocol (HTTP). A request may be received via a secure connection. For example, a request may be received over hypertext transfer protocol secure (HTTPS). In one embodiment, a request is received over a virtual private network (VPN) connection. A request may be received through one or more application programming interfaces (APIs). In an embodiment, a request is received from a website associated with a lab management organization, a healthcare provider, or a third-party. A request may be received in any number of languages or in any number of formats including, but not limited to, ActionScript®, AJAX, ASP, C, C++, HTML, JAVA JavaScript, JSON, JSP, MXML, PHP, XML, or XSLT. In embodiments, a request may be received from one or more data stores. For example, a request may be received from a data store associated with a healthcare provider. A request may be in an archive or compressed format, or both, such as JAR, ZIP, RAR, ISO, or TAR. A combination of protocols, languages, formats, and/or devices may be used to send or receive a request according to various embodiments.

A request may include various criteria. In one embodiment, a request includes identification information that identifies the electronic device making the request. For example, the identification information can include any information that enables the receiving device to determine the identity of the sending device. As one example, referring to FIG. 1, a request sent from desktop computer 115 and received by server 190 may include information, such as an IP address of the desktop computer 115, that allows the server 190 to communicate with the desktop computer 115. A request can include an identification of the party sending the request. For example, a request may contain a requestor's name, an associated organization such as the name of the organization that the requestor is affiliated with, an account number, a digital certificate, a username and password, a unique identification number, a billing address, a mailing address, one or more phone numbers, other contact information, other authentication information, or a combination thereof.

In one embodiment, a request includes all the information needed to process a request. For example, referring to FIG. 1, a request received by server 190 from tablet computer 130 is received through a VPN connection and includes all the information necessary for the server 190 to process the request. A request may include information associated with one or more laboratory tests that need to be ordered. For example, a request may include lab testing information such as a lab test name, a lab test reference number, a timeframe for which results are needed, one or more patient names for which a lab test is needed, or other lab testing information. In embodiments, patient information such as a patient's name, address, phone number, employer, healthcare provider, healthcare physician, health plan provider, health plan name, health plan number, or other patient-related information can be received in a request. A request may contain payment information for one or more lab tests. Additional information that may be received in a request is disclosed herein or will be obvious to one of skill in the art.

In embodiments, a request may be received through a reiterative process. For example, an initial request may include authentication information. In this embodiment, the request may be authenticated as described in block 420 and, if the authentication is successful, additional information may be presented to the requestor to complete the request. For example, the initial request may include a username and password which is used by server 190 to determine whether the requestor is authorized to submit a request. In this embodiment, the server 190 may access data store 195 to determine whether the username and password provided in the request matches information stored in the data store 195 and, thus, whether the requestor is authorized to submit a request. If a determination is made that the requestor is authorized to submit a request, then additional information may be sent to a device associated with the requestor. For example, if a nurse associated with doctor's office 110 submits a request, including a username and password, to server 190 from desktop computer 115 and the server 190 determines that the nurse is authorized to submit a request, then additional information may be sent to the desktop computer 115.

In one embodiment, the additional information includes a form that can be used to complete the submission of a request. The form may be a web-based form or a web-based application. For example, the nurse may be presented with a form asking for information such as an ordering doctor's name, a patient's name, a lab test, etc. In one embodiment, as information is provided to the form various devices communicate with each other and information may be automatically filled in. For example, when the nurse selects a doctor's name then a list of patients associated with the doctor may be generated and displayed to the nurse. In one embodiment, a form includes one or more lab tests that can be selected for one or more patients. Possible laboratory tests that may be provided include, but are not limited to, one or more of the following: Allergen Profile(s); Calcitriol; Celiac Disease HLA DQ Association; Cystic Fibrosis (CF) Expanded Profile; Ferritin, Serum; Glucagon, Plasma; HLA A Disease Association; Amylase Isoenzymes, Serum; Amlase, Serum; C-Peptide (various); Cholesterol, Total; *Babesia microti*; Fine Needle Aspiration Cytology; Aerobic Bacterial Culture; Blood Culture; Creatinine, Serum; Fungus Culture; Urinalysis; Antineutrophil Cytoplasmic Antibody (ANCA) Profile; Cell Count, Synovial Fluid; *Chlamydia psittaci* Antibody; Adenovirus (various); Glucose (plasma or serum); Ferritin; Hemoglobin (Hb); Red Blood Cell (RBC) Count; Isocyanates Profile; and/or other laboratory test(s).

In an embodiment, the additional information includes a prioritized grouping of one or more lab tests. In one embodiment, one or more lab tests are based on a frequently ordered test group. For example, a doctor may have previously created a test group name and have selected one, two, three, or more lab tests to be associated with the test group name. In this embodiment, the additional information may include the test group name that can be selected to order each of the tests associated with the test group name. Multiple test group names may be associated with a doctor, office, hospital, or another healthcare provider. For example, in one embodiment, a first test group named "Test Group 1" is associated with a first lab test, a second, lab test, and a third lab test and a second test group name "Test Group 2" is associated with the second lab test and a fourth lab test. In this embodiment, each test group is associated with a particular doctor and when the doctor's name is selected as having authorized a laboratory test for a patient, then "Test Group 1" and "Test Group 2" are displayed as options that can be selected to order the tests in that group. For example, "Test Group 1" and "Test Group 2" may be presented in a drop down menu. In this embodiment, if "Test Group 1" is selected for a patient, then the first lab test, the second lab test, and the third lab test may be added to the order for the patient. Similarly, if "Test Group 2" is selected, then the second lab test and the fourth lab test may be added to the order. In one embodiment, if both "Test Group 1" and "Test Group 2" are ordered, then the duplicate test—the second lab test—will only be added to the order once for the patient. Thus, in various embodiments, a doctor, an office, a healthcare provider, a laboratory, and/or another participant in the laboratory benefit management system may be able to predefine test groupings which, when selected, can be used to order one or more lab tests.

In one embodiment, the additional information is prioritized based on a popularity of one or more tests. In an embodiment, the lab tests most frequently ordered by a participant in the laboratory benefit management system may be presented higher in a list of tests than less frequently ordered tests. For example, a list of most frequently ordered tests for a particular doctor may be presented when the particular doctor is determined to be associated with a request. In another embodiment, a drop down menu of frequently ordered tests for a particular office is presented when a determination is made that a request is associated with the office and/or a doctor in the office. A prioritized list of lab tests may be based at least in part on a healthcare provider, office, physician, region, laboratory, insurance provider, insurance plan, and/or another participant in a laboratory benefit management system.

In one embodiment, one or more prioritized lab tests are listed first and then other lab tests are listed. For example, one or more prioritized lab tests may be presented first in a drop down menu and the remaining available lab tests may be included in the drop down menu after the prioritized lab tests and ordered alphabetically. In another embodiment, one or more prioritized lab tests are listed in a single grouping. For example, a drop down menu may contain only the list of prioritized tests. In this embodiment, another drop down menu may provide a list of available lab tests. In various embodiments, one or more of the prioritized tests may be selected to add the lab test or lab tests to the order for one or more patients.

In another embodiment, when the nurse selects a patient's name one or more doctor's associated with the patient may be provided. Other information, such as the patient's address, phone number, and health plan information may automatically be filled in from one or more data sources. For example, information stored in a data store associated with doctor's office 110 may be accessed to automatically fill in at least a portion of the form. In one embodiment, as information is filled out such as on desktop computer 115, at least some of the information is sent to server 190. In this embodiment, server 190 may access data store 195 to determine whether information needed to fill out the form or other relevant information is available. If such information is available, then server 190 may send the additional information to the requesting device, desktop computer 115 in this case. The requesting device may use at least a portion of the additional information received from the server 190 to automatically fill in at least a portion of the form.

In embodiments, additional information received from server 190 related to data entered in a form may be shown. For example, a list of previous tests and test results that a patient has received may be sent from server 190 to desktop computer 115 and this information may be displayed on the desktop computer 115 to help a nurse completing a request complete the form by informing the nurse of previous medical information for the patient. Information may be exchanged via the various devices using one or more asynchronous or synchronous programming languages.

Figure 7:
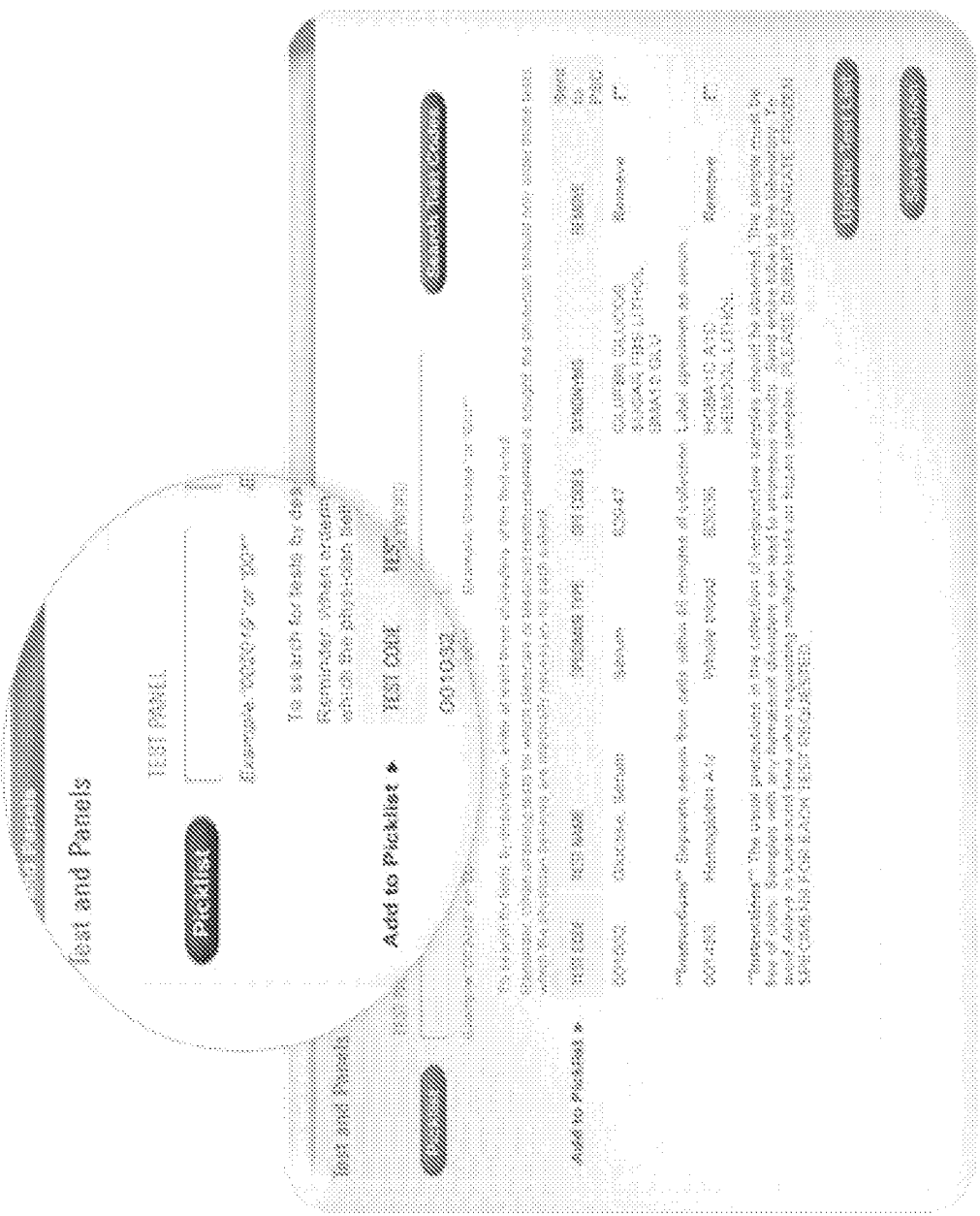
FIG. 7 is a screenshot of an order entry form according to an embodiment.

FIG. 7 shows a screenshot of an order entry form according to one embodiment. In FIG. 7, a lab test can be selected for a patient by entering the test code for the lab test in the Test Panel text box. A lab test may also be selected for a patient by entering a keyword in the Keyword text box and searching for an appropriate lab test. Furthermore, in FIG. 7, the "Picklist" button can be selected. In this embodiment, when the Picklist is selected, information regarding one or more lab tests may be displayed that can be selected. For example, a list of the most commonly ordered tests for the healthcare provider associated with the order may be listed. As another example, one or more test groupings of predetermined lab tests may be presented for the healthcare provider associated with the order.

Referring back to FIG. 4, once a request has been received 410 the method 400 proceeds to block 420. In block 420, the request is authenticated. Authentication may be performed in any number of ways. In one embodiment, a request includes a username and password that is used to authenticate the request. For example, referring to FIG. 1, if a request is received by server 190 and includes a username and a password, then this information may be compared to a database of usernames and passwords in data store 195 to determine whether the request should be allowed. A request may be authenticated by using a digital certificate which verifies the identity of the requestor. In embodiments, a security token, fingerprint, retinal pattern, voice phrase, personal identification number, one or more challenge questions, a code provided to the requestor, or other authentication may be used to authenticate a request.

Referring back to FIG. 4, once a request is authenticated 420, the method 400 proceeds to block 430. In block 430, eligibility is determined. Eligibility may be determined in any number of ways. In one embodiment, eligibility is determined based on information contained in a request and data stored in one or more data stores. For example, referring to FIG. 1, a request sent from hospital 120 to server 190 may include patient identification information such as a unique patient identification number. In this embodiment, server 190 receives the request and accesses information in data store 195 to determine a health plan provider associated with a patient having the unique patient identification number. Using this information, the server 190 may access one or more data stores to determine whether the patient is eligible to receive one or more lab tests provided in the request. For example, server 190 may query data store 195 to determine whether the patient having a particular health plan provider or a particular health plan, or both, is eligible to receive one or more lab tests. In another embodiment, the server 190 may query an external data store, such as data store 285 shown in FIG. 2, to make a determination as to whether a patient is eligible to receive one or more lab tests.

In embodiments, one or more rules and/or preferences may be applied to a request to determine whether one or more tests associated with the request are eligible to be ordered. In one embodiment, one or more internal rules are applied to determine whether at least a portion of a request associated with an order meets eligibility requirements. For example, in one embodiment, a request is associated with three laboratory tests for a patient. In this embodiment, a rule is applied to the three laboratory tests to determine whether any of the tests is a duplicative lab test. In one embodiment, if one or more of the laboratory tests are duplicative, then an alert may be sent to the requesting device. In one embodiment, a user of the requesting device can override the alert, rule, and/or preference and continue ordering the duplicative tests for a patient. In another embodiment, a user of the requesting device cannot override the alert, rule, and/or preference and must change the laboratory tests associated with the request. In yet another embodiment, the rules automatically remove any duplicative tests associated with a patient in received in a request.

As another example, in one embodiment, a rule is applied to determine whether a patient associated with a request has a previous balance due. In an embodiment, if the patient has a balance due, an order for one or more lab tests for the patient cannot be ordered until the balance has been paid. In another embodiment, an alert is sent to the requesting device notifying a user of the device that a balance is due for the patient. The user may or may not be able to override the alert depending on the implementation. As yet another example, a rule can be applied to determine whether a lab test specified in a request is associated with a particular gender and, if so, compares the particular gender associated with the test with the gender of a patient for which the test is being ordered. For example, if a test is a male-specific test and the patient is a female, or vice versa, then an alert may be sent to the requesting device indicating that the lab test is associated with a gender that is different than the gender of the patient. In some embodiments, the user of the requesting device can override the alert and in other embodiments a request having a test associated with a gender different from the gender of a patient for which the test is being ordered cannot be overridden.

In various embodiments, one or more rules and/or preferences may be applied to at least a portion of a request from any number of participants in the laboratory benefit management system. As discussed above, one or more internal rules and/or preferences may be based at least in part on one or more internal rules and/or preferences created by an administrator of the laboratory benefit management system. In one embodiment, one or more rules and/or preferences are predefined for an insurance provider and/or a healthcare plan associated with a request and at least a portion of the predefined rules and/or preferences are applied to at least a portion of the request. In an embodiment, one or more rules and/or preferences can be predefined for a healthcare provider—such as a particular doctor, office, hospital, etc.—associated with a request and at least a portion of the predefined rules and/or preferences may be applied to at least a portion of the request. In another embodiment, one or more rules and/or preferences are defined based on a location, state, region, healthcare provider, insurance provider, insurance plan, internal specifications, other factors, or a combination thereof, and applied to at least a portion of a request to determine eligibility. Numerous additional embodiments are disclosed herein and variations are within the scope of this disclosure.

Numerous factors may be used to determine whether a patient is eligible to receive one or more lab tests. In one embodiment, a factor used to determine whether a patient is eligible to receive one or more lab tests is based on membership data. For example, server 190 may query data store 195 to determine whether a patient is currently an active member in a health plan for a health plan provider. If a determination is made that the patient is an active member in the health plan, then the patient may be determined to be eligible. If a determination is made that the patient is not currently an active member in the health plan, then the patient may be determined to be ineligible. Another factor used to determine whether a patient is eligible to receive one or more lab tests may be based on a timeframe since last having one or more lab tests. For example, sever 190 may query an external data store, such as data store 280 or 285, to determine whether a patient has previously had a particular lab test. In this embodiment, health plan data may be accessed to determine a member of the health plan is eligible to receive the lab test if the member has not had a similar lab test in the last sixty days. If results from one or more data stores indicates that the patient has had the same or a similar lab test within the last sixty days, then a determination may be made that the patient is ineligible to receive one or more lab tests. On the other hand, if results from one or more data stores indicates that the patient has not had the same or a similar test within the timeframe specified by the health plan provider, then the patient may be determined to be eligible to receive one or more lab tests.

One factor used to determine whether one or more tests are eligible to be ordered for a patient can be based on a previously-collected sample for a patient. For example, in one embodiment, a determination is made as to whether enough of a previously-taken sample for a patient remains to perform one or more lab tests specified in a request. In one embodiment, enough of a previously-taken sample for a patient must be available before one or more tests for a patient can be ordered. In another embodiment, if a sample has not previously been taken for a patient or if there is not enough of a usable sample available, then an alert is sent to the requesting device. The alert may provide an indication that a new or additional sample will be required from the patient in order for one or more of the lab tests to be performed. In one embodiment, a user of the requesting device can remove any lab test or tests that require an new or additional sample to be taken from a patient. In another embodiment, a user of the requesting device can proceed with ordering one or more tests requiring a new or additional sample for a patient.

Referring back to FIG. 4, once member eligibility is determined 430, the method 400 proceeds to block 440. In block 440, a physician's authorization is requested. In one embodiment, if a physician submits a request or if the authentication indicates that a physician is submitting a request, then the request may automatically be authorized. If, however, a physician associated with a patient for which one or more lab tests are being requested does not submit the request, then the physician may have to authorize the request. For example, a nurse associated with doctor's office 110 may submit a request for a lab test for a patient that was seen by a doctor in the doctor's office 110. In this embodiment, the doctor may receive a notification that authorization for one or more requests is required. A notification may be sent in any form including, but not limited to, a text message, an email, a fax, an automated phone call, or other electronic notifications. In one embodiment, the doctor may be able to access one or more web pages associated with the doctor that provides notification of requests that need to be authorized by the doctor. Information regarding requests that need to be authorized may be stored in data store 195. For example, data store 195 may contain a list of requests that need authorization as well as a list of users that need to authorize one or more of the requests.

Referring back to FIG. 4, once a physician's authorization is requested, the method 400 proceeds to block 450. In block 450, one or more tracking numbers for the order are created. For example, a request may contain information indicating that a patient associated with one doctor needs a particular lab test and additional information indicating that another patient associated with another doctor needs two other lab tests. In this embodiment, a unique tracking number is associated with each of the lab tests and, thus, three tracking numbers are created. In another embodiment, one tracking number may be created for the entire request. In one embodiment, a tracking number is created for each patient associated with the request. A tracking number may be created for each healthcare provider, such as hospital 120 or doctor's office 110, associated with a request. In one embodiment, a tracking number is created for each personnel member, such as a doctor, that is associated with a request.

Referring back to FIG. 4, once one or more tracking numbers have been created 450, the method 400 proceeds to block 460. In block 460, a physician's authorization is received. A physician's authorization may be received in any number of ways. In one embodiment, a physician may visit a website to authorize one or more requests. For example, a physician using desktop computer 115 associated with doctor's office 110 may send a request for a page of a website to sever 190 through network 105. The server 190 may receive the request and query data store 195 to determine whether there are any outstanding requests for which the physician needs to authorize. The server 190 may then send any outstanding requests needing authorization to the desktop computer 115 that the physician is using. Using the desktop computer 115, the physician may be able to select one or more requests to authorize and submit the authorization to server 190. In various embodiments, authorization may be received by a device, such as server 190, associated with a lab management organization through any number of ways. As discussed above, server 190 may receive authorization from a device accessing a website associated with a lab management authorization. Authorization may be received through an application programming interface (API) call. In various embodiments, one or more applications, such as a desktop application or a Windows®-based application or an application for a mobile device, may be executed that facilitates authorization for at least a portion of one or more requests. For example, tablet computer 130 associated with hospital 120 may execute an application that can be used by a physician to authorize at least a portion of a request. The application may be able to communicate with other devices, such as server 190, through network 105 and network 125.

Performance Privileging Component

Figure 5:
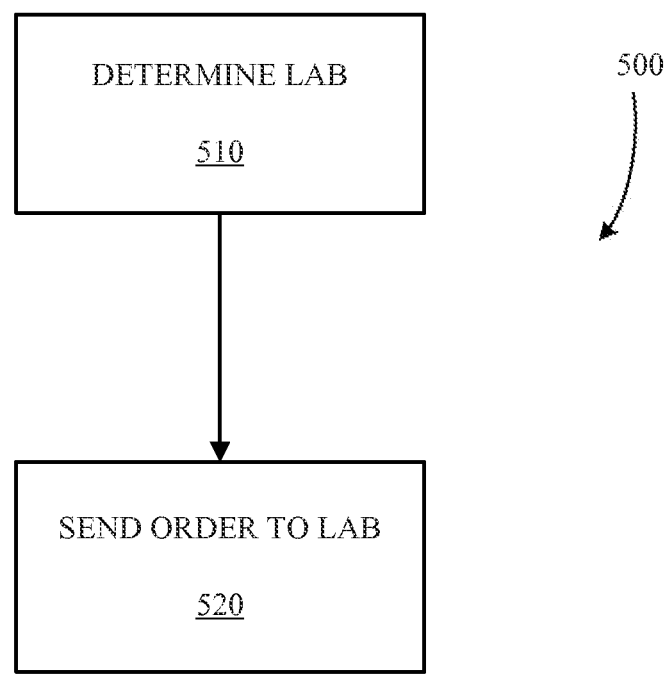
FIG. 5 is a flow chart illustrating a method for a performance privileging component of a laboratory benefit management system according to an embodiment.

FIG. 5 is a flow chart illustrating a method 500 for a performance privileging component of a laboratory benefit management system according to an embodiment. For example, one or more steps described with respect to method 500 may be performed in the performance privileging component 360 shown in FIG. 3. The description of method 500 will be made with respect to FIG. 1, which illustrates an example environment 100 for implementing aspects in accordance with various embodiments.

The method 500 begins when one or more labs are determined for one or more orders 510. One or more labs may be determined in any number of ways. In one embodiment, one or more labs are determined based on the test or tests requested in the order. For example, an order may request a first test and a second test for a patient. In this embodiment, a first lab may perform the first test, a second lab may perform the second test, and a third lab may perform both the first and the second test. In this embodiment, a determination may be made that the third lab should complete the first and second lab tests for this order because the third lab can perform both tests. In another embodiment, a determination may be made that the first lab should complete the first lab test and that the third lab should complete the second lab test because of one or more other factors disclosed herein. Furthermore, the second lab may not be chosen to complete the first lab test because the second lab does not perform the type of test requested in the first lab test.

In one embodiment, one or more labs are determined based on availability. For example, two labs may perform a lab test ordered for a patient. In this embodiment, however, the request may specify that results are needed within one week. One of the labs may have the capacity to complete the lab test within the one week timeframe and the other lab may not have the capacity to complete the lab test within the one week timeframe. In this embodiment, the lab that has the capacity to complete the lab test within the requested timeframe may be chosen to perform the lab test. One or more labs may be determined based on the location of the lab. For example, one lab testing facility may be closer to the healthcare provider that submitted the order than another lab testing facility. In this embodiment, the closer lab testing facility may be selected. Multiple labs may be selected for a single lab test. For example, one lab facility—such as a physician office lab—that is in close proximity to a patient may be chosen to collect a sample from the patient for the lab test while another lab facility is selected to analyze the sample. In one embodiment, one or more labs are determined based on whether the labs are in network or out of network. For example, if two labs are available to perform a lab test for an order and one lab is an in-network lab and the other lab is an out-of-network lab, then the in-network lab may be chosen over the out-of-network lab.

In embodiments, one or more labs are determined based on the cost for a lab test. For example, two labs may be available to perform a lab test related to an order. In this example, the first lab may charge $50 to perform the lab test and the second lab may charge $75 to perform the lab test. In this embodiment, the first lab may be chosen because it would be more profitable for the lab management organization to pay $50 to perform the test than $75. In embodiments, one or more labs are determined based on the profitability for a lab test. For example, two labs may be available to perform a lab test related to an order. In this example, the first lab may charge a price such that the profitability to the lab management organization would be 35% if the first lab was chosen to perform the lab test. The second lab may charge a price such that the profitability to the lab management organization would be 40% if the second lab was chosen to perform the lab test. In this embodiment, the second lab may be chosen to perform the second lab test based on the higher profitability for the lab management organization.

In one embodiment, one or more labs may be determined based on an overall profitability. A lab management organization may receive a discount if a number of lab tests are ordered within a period of time. For example, the lab management organization may receive a discount if twenty lab tests are ordered within a month from a particular testing facility. In this embodiment, nineteen lab tests may have been ordered so far in a particular month and an order for two additional lab tests may be received by the lab management organization. One of the lab tests may be chosen to be performed by the testing facility so that the discount is received for the month. In embodiments, the testing facility is chosen even though the profitability for the one test is lower than the profitability at another testing facility because the overall profitability is higher for all the orders because of the discount for reaching twenty tests in a month.

In embodiments, one or more labs may be based on a combination of factors. For example, one or more testing facilities may be determined based on services offered, availability, location, cost, profitability, whether the lab is an in-network or out-of-network lab, or a combination thereof. In embodiments, one or more lab testing facilities may be determined based at least in part on statistical information related to one or more testing facilities. For example, one or more labs may be determined based on the accuracy, reliability, or other statistics associated with a lab.

In an embodiment, one or more rules and/or preferences may be applied in determining one or more labs to perform the lab test or tests associated with an order. In one embodiment, one or more predefined rules and/or preferences from a doctor authorizing an order are applied in determining one or more labs to perform the lab test or tests associated with the order. For example, the doctor may specify a preferred laboratory, turnaround time, location, etc. that is used, at least in part, by the laboratory benefit management system to determine one or more laboratories to perform the test or tests associated with the order. In various embodiments, one or more rules and/or preferences from a healthcare provider such as a doctor, department, office, etc., insurance provider, laboratory, and/or internal system rules and/or preferences are applied to at least a portion of an order to determine one or more labs to perform the tests associated with the order. The rules and/or preferences can be based on any number of factors including, but not limited to, locations, states, regions, healthcare providers, insurance provider, insurance plans, laboratories, time, availability cost, and/or other factors. Numerous additional embodiments are disclosed herein and variations are within the scope of this disclosure.

Referring back to FIG. 5, once one or more labs have been determined for an order 510, the method 500 proceeds to block 520. In block 520, at least a portion of the order is sent to one or more of the determined labs. Sending at least a portion of an order to one or more labs may comprise sending a notification to a lab. A notification may be sent in any form including, but not limited to, a text message, an email, a fax, an automated phone call, or other electronic notifications. In one embodiment, a lab testing facility may be able to access one or more web pages associated with the lab management organization that provides notification of orders. Information regarding orders may be stored in a data store, such as data store 195 shown in FIG. 1. For example, data store 195 may contain a list of completed orders as well as a list of pending orders that need to be completed.

Lab Testing Component

Figure 6:
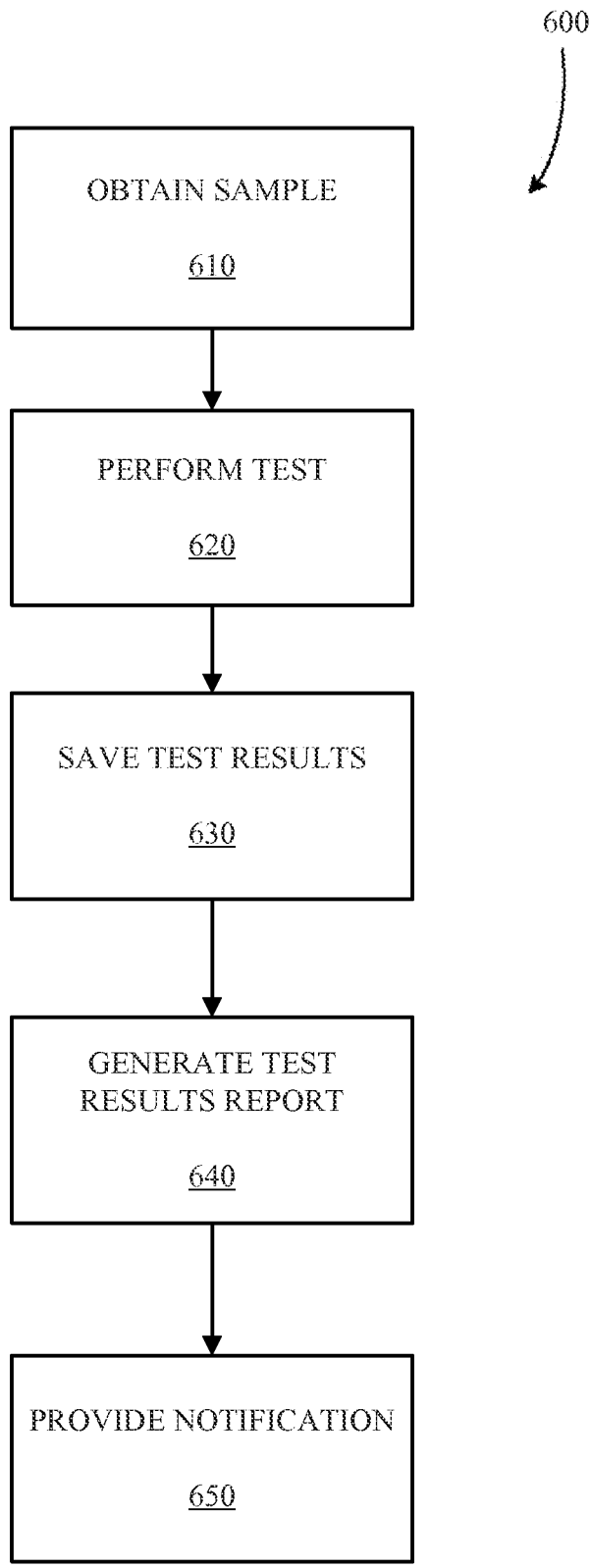
FIG. 6 is a flow chart illustrating a method for a lab testing component of a laboratory benefit management system according to an embodiment.

FIG. 6 is a flow chart illustrating a method 600 for a lab testing component of a laboratory benefit management system according to an embodiment. For example, one or more steps described with respect to method 600 may be performed in the lab testing component 370 shown in FIG. 3. The description of method 600 will be made with respect to FIG. 1, which illustrates an example environment 100 for implementing aspects in accordance with various embodiments.

The method 600 begins in block 610 when a sample is obtained. For example, one or more samples for a patient may be obtained from a doctor's office. In other embodiments, one or more samples are obtained from a patient in a healthcare facility, laboratory, or another sample collection facility.

In an embodiment, the laboratory benefit management system provides information regarding the collection of one or more samples to be collected from a patient. For example, in one embodiment, personnel at a sample collection facility—such as a doctor's office, hospital, laboratory, etc.—can enter an order number associated with a patient and receive information regarding the collection of one or more samples.

As another example, personnel at a sample collection facility can enter information to identify a patient, such as a patient's social security number, name, birth date, address, etc., and receive information regarding the collection of one or more samples for an order. The collection information regarding the collection of one or more samples can include information such as sampling order, tube type, tube size, top color, collection quantity, collection type, other collection instructions, handling instructions, shipping instructions, and/or other information configured to make collection of one or more samples easier, clearer, and/or more accurate.

Information regarding the collection, handling, and/or shipping of one or more samples may be based on one or more participants in the laboratory benefit management system. In one embodiment, internal rules and/or preferences specified by an administrator of the laboratory benefit management system are used to determine at least a portion of the information. In an embodiment, rules and/or preferences specified by a particular laboratory that will be conducting a lab test are used to determine at least a portion of the information provided to a collection facility. For example, a first laboratory and a second laboratory may both be capable of conducting a particular lab test. In this embodiment, the first laboratory requires a 5.0 mL sample to be collected in order to conduct the particular lab test. In addition, in this embodiment, the first laboratory also requires that the sample be placed in a tube having a blue top and that the tube be filled to 85 percent capacity. The second laboratory may require that a 6.0 mL sample be collected and that the tube have an orange top. In this embodiment, the information sent to a device associated with the collection facility regarding the collection of the sample for the particular lab test, depends at least in part on whether the first laboratory or the second laboratory will be conducting the lab test. Thus, if the first laboratory will be conducting the particular lab test, then the information provided regarding the collection of the sample includes instructions that at least 5.0 mL needs to be collected, that the tube needs to have a blue top, and that the tube needs to be filled to 85 percent capacity. Similarly, if the second laboratory will be conducting the particular lab test, then the information provided regarding the collection of the sample includes instructions that at least 6.0 mL needs to be collected and that the tube should have an orange top. Numerous additional embodiments are disclosed herein and variations are within the scope of this disclosure.

In embodiments, one or more rules and/or preferences from any number of participants in the system may be used to determine information regarding the collection, handling, and/or shipping of one or more samples. For example, as discussed above, one or more rules and/or preferences may be specified for a particular laboratory in the system and/or one or more internal rules and/or preferences may be applied to determine information regarding the collection, handling, and/or shipping of one or more samples. In other embodiments, rules and/or preferences from doctors, offices, hospitals, other healthcare providers, laboratories, insurance providers, and/or other participants in the laboratory benefit management system may be applied to determined information regarding the collection, handling, and/or shipping of one or more samples for an order. In some embodiments, rules and/or preferences from two or more participants—such as a particular doctor, a particular lab, and internal specifications—may be applied to a particular order to determine how one or more specimens should be collected, handled, and/or shipped.

In one embodiment, information regarding the collection, handling, and/or shipping of one or more samples is based at least in part on a consolidation of multiple laboratory tests for a patient. In an embodiment, if one or more orders for a patient have a combined two or more outstanding laboratory tests that require a same type of sample, then these tests may be consolidated for specimen collection purposes. For example, if a lab order for a patient contains three lab tests and the first lab test requires a 2.0 mL collection of blood, the second lab test requires a 3.0 mL collection of blood, and the third lab test requires a 2.5 mL collection of blood, then information regarding the specimen collection for the patient may include instructions to collect 7.5 mL of blood. In one embodiment, the consolidation is based at least in part on one or more laboratories that will be conducting the lab tests. For example, using the example above, if a first laboratory will conduct the first and the third lab tests and a second laboratory will conduct the second lab test, then information regarding the specimen collection for the patient can include instructions to collect 4.5 mL of blood in a first tube to send to the first laboratory and 3.0 mL of blood in a second tube to send to the second laboratory. Numerous additional embodiments are disclosed herein and variations are within the scope of this disclosure.

In one embodiment, information regarding the collection, handling, and/or shipping of one or more samples is based at least in part on previously collected samples. For example, if a 6.0 mL sample has previously been collected from a patient to conduct a previous lab test that required 2.0 mL of the sample, and 3.0 mL of the same type of sample is needed to conduct a newly ordered lab test, then a specimen collection for the newly ordered lab test may not be needed because of the previous collection. Thus, in embodiments, the laboratory benefit management system can inventory the amount of one or more samples and use this information to determine whether additional samples are needed. In some embodiments, the laboratory benefit management system can track additional information such as how long a specimen can be used for testing purposes, the quantity of one or more specimens, the quantity of a specimen required by particular labs, or other information usable by the system to determine collection, handling, and/or shipping instructions for one or more laboratory tests. In one embodiment, a laboratory is selected based at least in part on the quantity of previously collected specimen that remains for a patient and the amount of specimen required by one or more labs to complete a particular lab test. For example, using the example above, if 4.0 mL of a sample remains after a first lab test has been conducted and another lab test using the same type of sample is ordered, then a laboratory that requires 4.0 mL or less of the sample in order to complete the other lab test can be selected. Numerous additional embodiments are disclosed herein and variations are within the scope of this disclosure.

A sample collected from a patient at one facility may be sent to one or more laboratories through a carrier such as FedEx or UPS. The sample may contain information associating the sample with a patient, one or more orders, one or more lab tests, or a combination thereof. For example, a sample may contain a barcode that is used to determine a lab order that the sample is associated with. In one embodiment, a sample may contain information so that the location of the sample can be tracked. For example, by scanning a barcode associated with the sample, the present or historical location, or both, of the sample may be accessed. Information related to a sample may be stored in one more data stores. In one embodiment, a sample is associated with a barcode. In this embodiment, the barcode is stored in data store 195. Other information such as one or more tests that the sample will be used for, a patient's name, testing facility, one or more locations, or other information related to the sample may be stored in data store 195. Various devices may be able to access information associated with a sample based on information supplied with the sample. For example, an internal lab 170 may be able to track the current location of a sample by entering tracking information associated with the sample into a website shown on desktop computer 175. In this embodiment, desktop computer 175 may send a request to server 190 through network 105. In response to receiving the request, server 190 may query data store 195 for information associated with the sample. For example, data store 195 may contain a present location for the sample, the name of a patient associated with the sample, and one or more tests that will be conducted using the sample. In embodiments, some or all of this information may be sent to the requesting device. Thus, server 190 may send a response to desktop computer 175 through network 105. In other embodiments, an application being executed on desktop computer 175 may be used to access information related to one or more samples.

Figure 8:
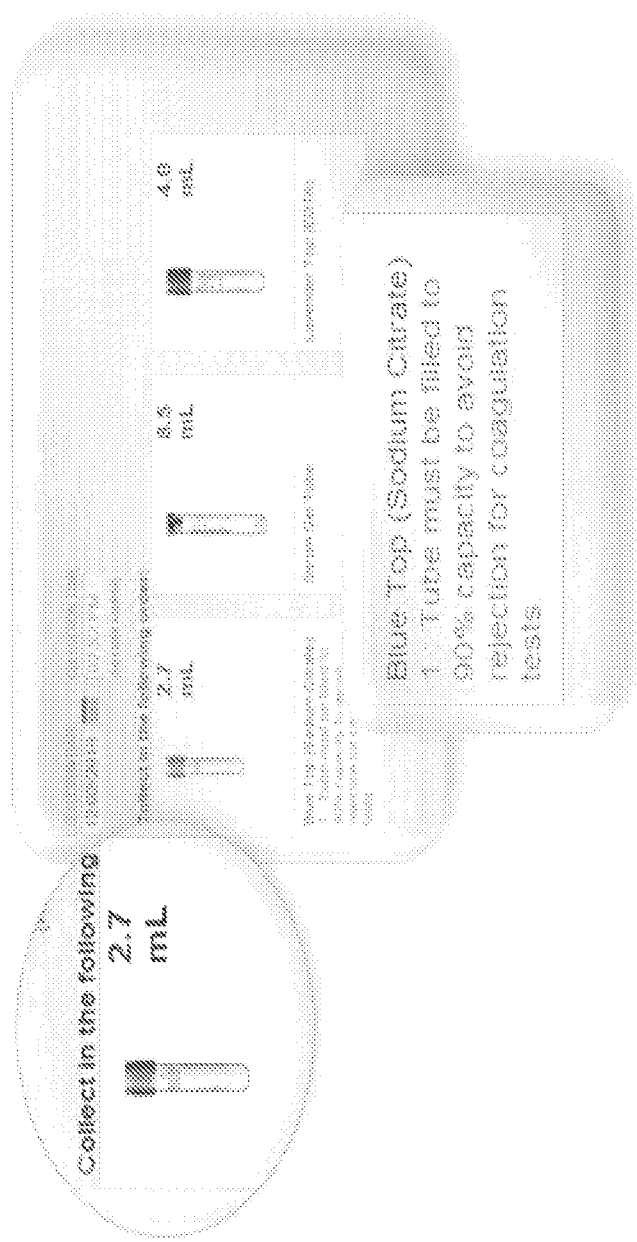
FIG. 8 is a screenshot of instructions for obtaining samples according to an embodiment.

FIG. 8 provides a screenshot of instructions for obtaining samples according to an embodiment. In the embodiment, shown in FIG. 8 three specimens need to be collected from a patient in a specific order. According to FIG. 8, a 2.7 mL specimen needs to be collected first and put into a tub having a blue top. In addition, the instructions specify that the tube must be filled to 90% capacity to avoid rejection for coagulation tests. The second specimen that needs to be collected in FIG. 8 is an 8.5 mL specimen that needs to be placed in a Serum Gel Tube. Finally, a 4.0 mL specimen needs to be collected and placed in a tube having a lavender top. Thus, FIG. 8 describes instructions for obtaining samples according to one embodiment. In other embodiments, additional and/or other instructions may be shown regarding the collection of one or more samples. In addition, or alternatively, instructions for handling and/or shipping one or more samples are provided in various embodiments. Numerous additional embodiments are disclosed herein and variations are within the scope of this disclosure.

Referring back to FIG. 6, once a sample has been received by the lab 610, the method 600 proceeds to block 620. In block 620, one or more tests are performed. Information relating to the status of one or more tests may be updated to reflect a current status of the test. For example, when a sample is initially received, a status of "Received By Lab" may be assigned to the sample. In this embodiment, when the lab test is started, the status of the test associated with the sample may be updated to reflect that the lab test has started. For example, the status of the lab test may be "Started" or "In Progress" or "Begun". In some embodiments an expected completion date may be created or updated. For example, an expected completion date may have previously been determined. In this embodiment, the expected completion date may be updated based at least in part on the actual starting date of the test. Information regarding the status of one or more tests or other information associated with performing one or more tests may be stored in one or more data stores. Referring to FIG. 1, such information may be stored in data store 195. In some embodiments, information may be stored in a data store external to the lab management organization such as lab data store 290 shown in FIG. 2. Various devices may query one or more data stores containing information related to the status of one or more tests.

Referring back to FIG. 6, once one or more tests have been performed 620, the method 600 proceeds to block 630. In block 630, the results for one or more tests are saved. Test results may be saved in any number of ways. In one embodiment, test results are saved electronically to one or more data stores For example, test result information may be saved to data store 195 shown in FIG. 1. Test result information may be saved to an external data store such as data store 290 shown in FIG. 2. Test result information may be saved in any format including, but not limited to, numerical data, plain text, HTML, XML, DOC, DOCX, PDF, XLS, etc. In one embodiment, test result information may be stored in a proprietary format. Other information such as historical medical information, various statistics, established medical guidelines, potential courses of action, potential diagnoses, customization settings, notification settings, authentication information, demographic information, medical literature, or other information useful in generating a test results report may be stored in one or more data store.

In embodiments, one or more notifications may be provided that indicate that test result information is available. For example, a notification may be sent to a healthcare provider or a physician, or both, and the notification may indicate that one or more test results for a patient associated with the healthcare provider or physician are available. A notification may be provided to a patient associated with the lab test. In one embodiment, a test results report may automatically be sent to a healthcare provider, physician, patient, or a combination thereof when test results are saved. As discussed herein, test results reports may be customized. Thus, customized test results reports may be sent to various parties. A notification or test results, or both, may be sent in numerous ways. For example, a notification or test results may be sent via email, SMS, or an automated telephone call. A notification may be provided in response to a received request. For example, server 190 may receive a request for one or more outstanding notifications. In this embodiment, server 190 may query data store 195 to determine whether there are any outstanding notifications. If one or more notifications are outstanding, then sever 190 may send at least a portion of the notifications to a device that requested the notifications. A notification may be provided to a website or an application being executed on a user device. Variations are within the scope of this disclosure.

Referring back to FIG. 6, once one or more test results have been saved 630, the method 600 proceeds to block 640. In block 640, one or more test results reports are generated. Test results reports may be generated in any number of ways. In one embodiment, the results of one or more tests is provided in response to a request from a device in communication with the lab management organization. For example, tablet computer 130 may send a request to server 190 through network 105 and network 125 that indicates that a user of the tablet computer 130 wants to view the results of one or more tests. In this embodiment, server 190 receives the request. Server 190 may query data store 195 for the requested test results or other medical information needed to customize the test results report. In one embodiment, data store 195 contains a document—such as an HTML file, a DOC file, a DOCX file, or a PDF file—that the server 190 can send to the tablet computer 130. In other embodiments, data store 195 contains test results data or other medical information, such as information used to customize a test results request. In this embodiment, server 190 queries data store 195 and uses at least some of the information received from data store 195 to generate a customized test results report. The server 190 can send the customized test results report to the table computer 130. A test results report may be sent in any number of formats including, but not limited to, numerical data, plain text, HTML, XML, DOC, DOCX, PDF, XLS, etc. In one embodiment, test results information may be stored in a proprietary format. In another embodiment, information related to one or more test results is sent to one or more applications being executed on a user device. For example, server 190 may send one or more test results reports to an application on desktop computer 115.

Test results reports may be provided at various times to one or more users of the laboratory benefit management system once test results have been saved. Tests results may automatically be sent to one or more users. For example, a doctor associated with hospital 120 may receive test results for one or more lab tests as soon as the results become available. Another physician associated with doctor's office 110 may receive test results on a periodic basis such as once per hour, once per day, every Monday, every four hours, or some other periodic timeframe. In some embodiments, test results are received based on a priority of the results. For example, in one embodiment, a doctor's office receives any critical test results immediately and receives other test results on a nightly basis. As another example, a physician may receive a test result immediately if the result for a particular lab test type is above a predetermined threshold. Various entities and users may be able to customize the delivery of tests results reports so that they receive reports at times specified by the entity or user.

In an embodiment, one or more test results are delivered to a single device, such as a desktop computer, laptop computer, or a mobile device. In another embodiment, one or more test results are delivered to multiple devices. For example, in one embodiment, critical test results are sent to an authorizing physician's tablet computer and non-critical test results are sent to a desktop computer in the physician's office. A determination regarding whether to send one or more test results to a particular test and/or the timing for sending one or more test results may be based on preferences specified by a physician, office, healthcare facility, and/or other participants in the laboratory management system.

In one embodiment, a single lab test result is sent in a report. In other embodiments, multiple lab tests results may be sent in a single report. For example, a combined lab test result report comprising the test results for each of the lab tests from one or more lab orders may be included in a single report. In one embodiment, a combined lab test result report covers multiple patients, physicians, offices, and/or healthcare providers. A combined test results report can include the test results for each patient associated with a particular healthcare provider over a period of time. For example, a combined nightly report may include the test results for each patient associated with a particular office that has not previously been reported. As another example, a combined weekly report may include the test results for each patient of a particular physician for which test results have been received over the previous week. Numerous additional embodiments are disclosed herein and variations are within the scope of this disclosure.

A test results report can contain information for the current lab test as well as information for various demographics. For example, a test results report may compare the current test results with test results for an overall population. A test results report may compare the current test results with test results from other patients having one or more similar circumstances including, but not limited to, the same age range, the same gender, the same weight, the same height, one or more common symptoms, one or more common illnesses, one or more common other lab tests, other medical information, or a combination there. Thus, a test results report may compare a patient's current lab tests results with various statistical information associated with other lab tests.

In one embodiment, at least a portion of the information contained in a test results report can be compared with other test results. For example, in one embodiment, a test results report includes the results of a current lab test for a patient as well as historical results of the same test for the patient. In another embodiment, a test results report includes the results of a current lab test for a patient as well as historical results of any number of tests for the patient. In some embodiments, the results for one or more tests may be provided in a textual manner and in other embodiments the results for one or more tests can be provided in a graphical manner, such as a pie chart, bar chart, line graph or other graphical depiction. In one embodiment, the test results report includes both textual and graphical representations for at least a portion of the results report.

At least a portion of the information contained in a test results report may compare a test result with information from one or more other patients. For example, in one embodiment, a physician can compare a test result for a lab test for a patient with another test result for the lab test for another patient. In an embodiment, one or more test results for a patient can be compared with a group or population of patients having one or more test results for the same and/or a similar type of lab test. For example, a test result for a patient may be compared with test results of other test results from other patients that match a particular demographic profile. In embodiments, a demographic profile may be based at least in part on age, gender, race, health issue, location, state, region, and/or other demographic information. In one embodiment, a test results report may include a comparison with other patients of a physician that authorized the lab test, other patients within an office associated with the physician, and/or other patients within a healthcare provider associated with the physician. In other embodiments, a test results report includes a comparison with all or a portion of the entire population of patients associated with the laboratory benefit management system. Thus, in embodiments, test results reports can include information across healthcare providers, laboratories, and/or health insurance providers. Numerous other embodiments are disclosed herein and variations are within the scope of this disclosure.

In embodiments, a test results report may contain one or more additional recommended tests. For example, based at least in part on the results of the current lab test, a determination may be made that one or more additional lab tests should be performed. A determination that one or more additional tests are recommended can be based on various sources of medical information. In one embodiment, a determination is made based at least in part on the results of other lab tests, such as the results of the same type of lab tests that were conducted on other samples or other related lab tests. In another embodiment, a determination is made based at least in part on medical history for the patient. One or more tests may be recommended based on evidence based guidelines. In some embodiments, one or more additional tests may be recommended based on other medical literature.

In embodiments, a test results report can contain potential diagnostic information. For example, a potential diagnosis may be determined based at least in part on the results of the current lab test. A potential diagnosis may be determined based on various sources of medical information. In one embodiment, a determination is made based at least in part on the results of other lab tests, such as the results of the same type of lab tests that were conducted on other samples or other related lab tests. In another embodiment, a determination is made based at least in part on the medical history for of patient, such as previous test results for the patient. One or diagnoses may be based on evidence based guidelines. In some embodiments, one or more diagnoses may be based on medical literature.

In embodiments, a test results report may contain one or more potential courses of action. For example, a potential course of action may be determined based at least in part on the results of the current lab test. A potential course of action may be determined based on various sources of medical information. In one embodiment, a potential course of action may be determined based at least in part on the results of other lab tests, such as the results of the same type of lab tests that were conducted on other samples or other related lab tests. In another embodiment, a potential course of action may be determined based at least in part on the medical history of the patient, such as previous test results for the patient. One or more potential courses of action may be based on evidence based guidelines. In some embodiments, one or more potential courses of action may be based on medical literature.

One or more entities or users may be able to customize the information contained in one or more test results report. For example, a physician may be able to customize test results reports so that only raw test results data is provided in a test results report. In another embodiment, a user can customize test results reports to include historical medical information related to a patient for which a lab test was performed. For example, a tests results report may contain results of the current lab test as well as the results of previous lab tests for the patient. In one embodiment, current test results or historical tests results, or both, may be provided in a graphical format. For example, one or more bar charts or line charts may be included in a tests results report that graphically demonstrate information related to the lab test. In some embodiments, one or more test results reports may be customized to include demographic information, additional recommended tests, potential diagnostic information, potential courses of action, other medical information, or a combination.

In embodiments, one or more entities or users may be able to control the level of customization. For example, referring to FIG. 1, hospital 120 may determine that physicians associated with the hospital can choose whether or not a test results report includes additional recommended tests or potential diagnostic information, but that physicians cannot receive test results reports that contain potential courses of action. In this embodiment, one physician associated with the hospital 120 can choose to receive a test results report that includes both additional recommended tests and potential diagnostic information. Another physician associated with hospital 120 may choose to receive test result reports that include additional recommended tests. In this embodiment, however, neither physician associated with hospital 120 can receive a test results report that includes potential courses of action because hospital 120 has disabled this option. In other embodiments, hospital 120 may let each physician associated with hospital 120 customize a test results report in any available manner. Thus, in embodiments, a level of allowable customization is based on a hierarchy of entities or users, or both.

In an embodiment, a patient for which a lab test was conducted can receive the results of the lab test. In one embodiment, the patient can customize the test results report as disclosed herein. In other embodiments, a healthcare provider may determine the information that a patient receives in a test result report. The patient may receive the same test results report as a physician associated with the patient. Alternatively, a physician may receive one test results report for a lab test and the patient for which the lab test was performed may receive a different test results report. For example, the physician's test results report may contain one or more potential diagnoses as well as one or more recommended courses of action and the patient's test results report may contain the results of the lab test as well as the test results of other lab tests that were previously performed for the patient.

Figure 9:
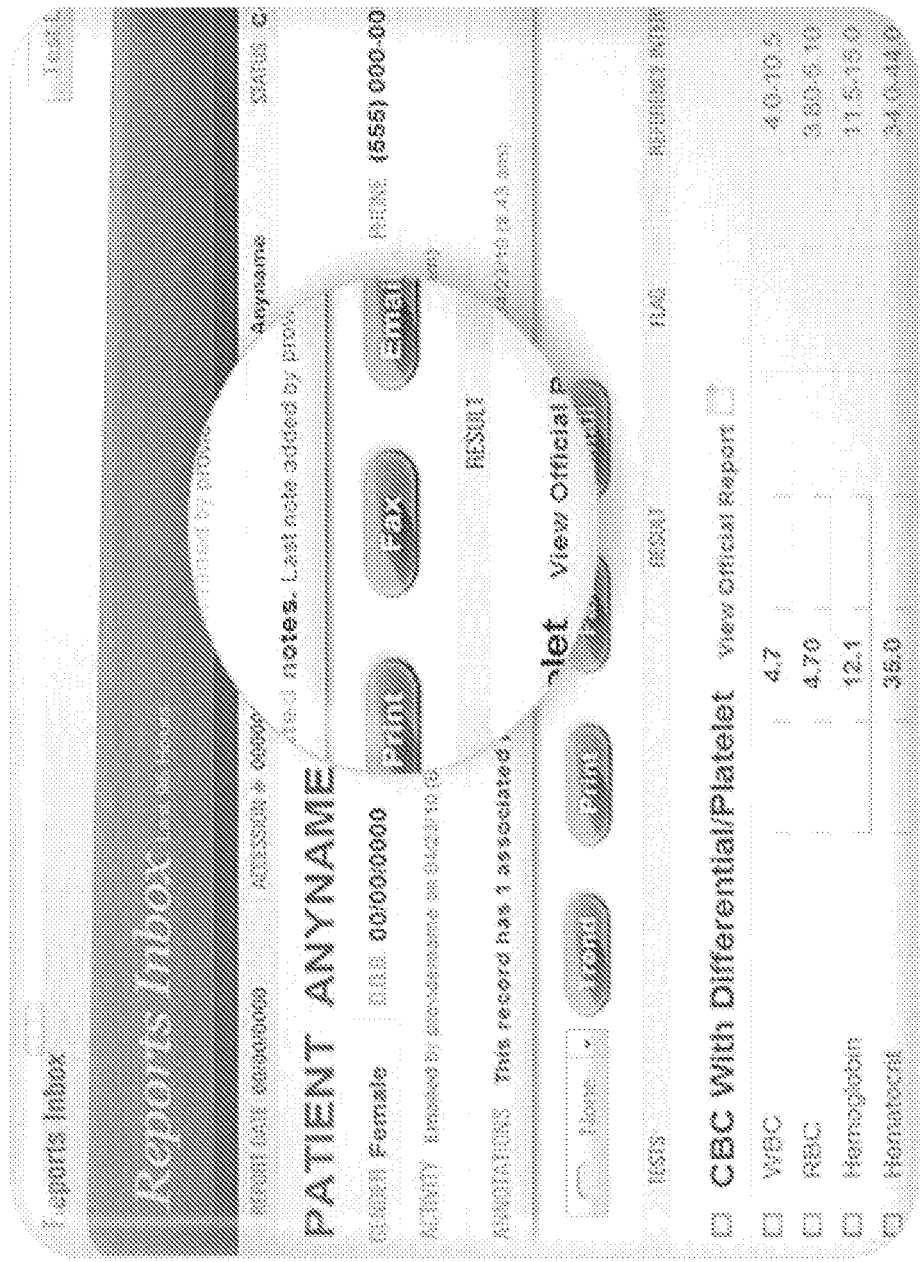
FIG. 9 is a screenshot of test results according to an embodiment.

FIG. 9 provides a screenshot of test results according to an embodiment. In the embodiment shown in FIG. 9, the test results report includes information usable to identify the patient. For example, the test report in FIG. 9 includes the patient's name, gender, date of birth, and phone number. In addition, the test results report includes several buttons that can be selected to perform various operations. For example, the "Trend" button may be selected to provide historical information for one or more test results for the patient. Furthermore, as discussed above, in embodiments the Trend information compares one or more test results with test results from other patients. Other buttons shown in FIG. 9 allow one or more test results for the patient to be printed, faxed, or emailed. In addition, the test results report in FIG. 9 provides the names of various lab tests that have been ordered for the patient and the results of the tests that have been completed. In some embodiments, the test results report includes reference results that may indicate a generally acceptable test result range for the results of a particular test.

Figure 10:
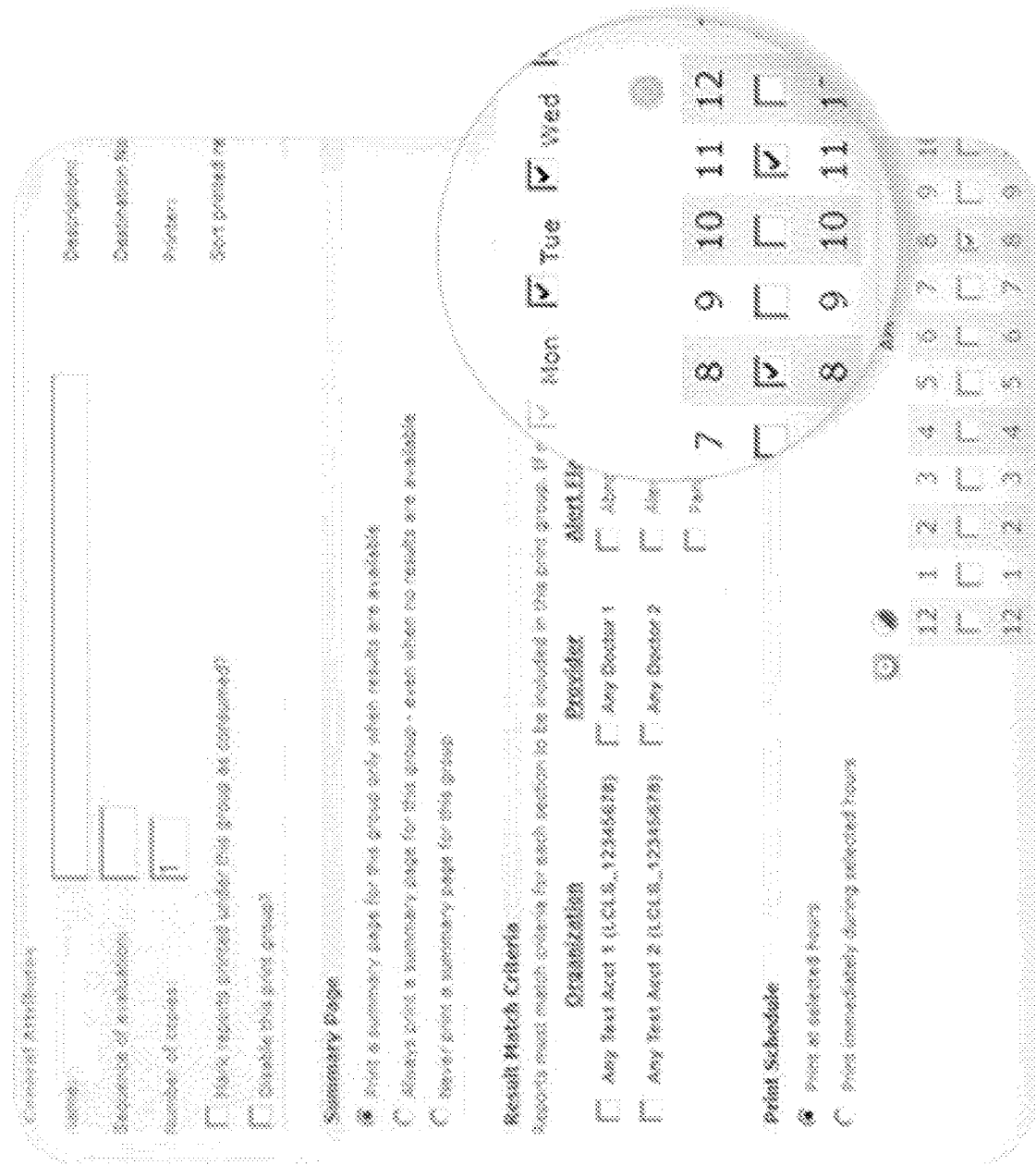
FIG. 10 is a screenshot of test result delivery options according to an embodiment.

FIG. 10 depicts a screenshot of test result delivery options according to an embodiment. In the embodiment shown in FIG. 10, a participant in the laboratory benefit management system can customize the delivery of test results. For example, in FIG. 10, a healthcare provider can customize how, when, and for whom test results should be reported. The customization may include a number of copies of a test result should be printed. In addition, as shown in FIG. 10, the format of a summary page, if any, can be selected by the healthcare provider. The customization can include a selection of one or more organizations, one or more providers, and/or one or more alert criteria as shown in FIG. 10. In one embodiment, test reports can be customized to be printed immediately on certain days and/or between certain times as test results are received by the laboratory benefit management system. In another embodiment, test reports can be customized to be printed at selected hours of selected days of the week.

Figure 11:
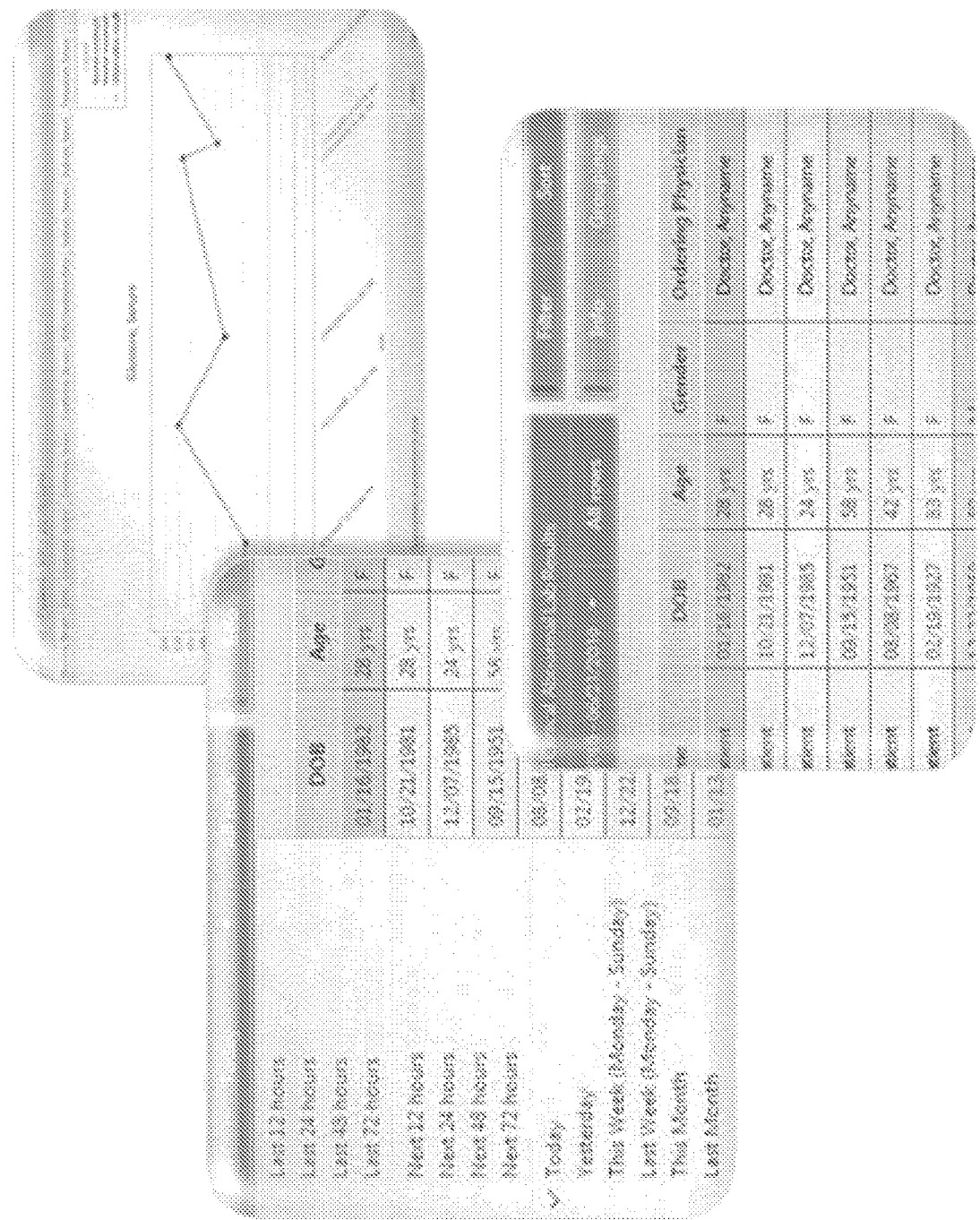
FIG. 11 depicts screenshots of result trending and analytics according to an embodiment.

FIG. 11 depicts screenshots of result trending and analytics according to an embodiment. As shown in FIG. 11, the test results for one or more tests can be graphed over a specified period of time. For example, the test results for one or more lab tests for one or more patients can be graphically shown for results received in the last 12 hours, last 48 hours, today, yesterday, or other periods of time. In the embodiment shown in FIG. 11, the graphical representation of one or more test results for one or more patients can be customized. For example, the test results for one or more patients can be sorted, filtered out, and/or grouped. Numerous other customizations are disclosed herein and variations are within the scope of this disclosure.

Figure 12A:
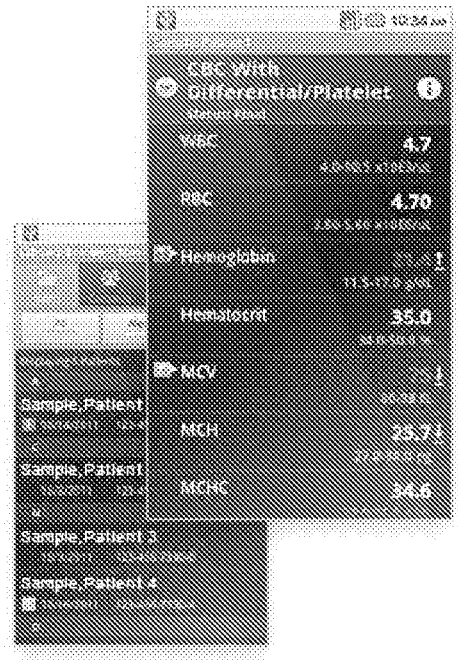
FIGS. 12A and 12B are screenshots of a mobile version of various aspects according to an embodiment.
Figure 12B:

FIGS. 12A and 12B provide screenshots of a mobile version of various aspects according to an embodiment. As shown in FIGS. 12A and 12B a mobile version can provide a physician with a list of patients associated with the physician. In this embodiment, the physician can select a patient from the list of patients to view the results of one or more lab tests associated with the patient. In various embodiments, a mobile version of the laboratory benefit management system can provide some or all of the features disclosed herein.

Referring back to FIG. 6, in some embodiments the method 600 proceeds to block 650. In block 650 of method 600, one or more notifications are provided. In one embodiment, one or more notifications are provided to a participant in the laboratory benefit management system in response to a problem with a specimen. For example, a notification may be provided to an authorizing physician, healthcare provider, and/or specimen collection facility if a sample fails to meet one or more of the collection, handling, and/or shipping instructions specified for a lab order. As one example, if the collected quantity of a specimen is too low to conduct a lab test, then a notification may be provided that indicates that another specimen needs to be collected. In another embodiment, one or more notifications are provided to a participant in the laboratory benefit management system in response to a billing problem associated with a lab order. For example, a notification may be provided to an authorizing physician and/or a physician's office if an insurance payment for a lab test is denied because the diagnostic code does not match an authorized diagnostic code for the lab test for the insurance provider. In this embodiment, the physician or physician's office may be able to update the diagnostic code so that the claim with the insurance provider can be successfully processed.

In one embodiment, one or more notifications are provided to a participant in the laboratory benefit management system for a reoccurring order. For example, a request for a laboratory test may indicate that the test should be performed on a periodic basis, such as every month, every other month, every six months, or every year. In another embodiment, one or more reoccurring lab tests may be ordered for a patient by a healthcare provider after receiving the results for one or more lab tests that were previously ordered. As the date for a reoccurring lab test approaches, the laboratory benefit management system can notify one or more participants in the system that the lab test needs to be performed. In one embodiment, the laboratory benefit management system notifies a healthcare provider that a patient needs to have a lab test. In another embodiment, the laboratory benefit management system can notify the patient that a lab test needs to be conducted. A notification may be provided in any number of ways. For example, a notification may be provided to a mobile phone, tablet computer, desktop computer, or other computing device. As another example, a notification may be provided via fax, email, text message, and/or to a printer.

General

Numerous specific details are set forth herein to provide a thorough understanding of the claimed subject matter. However, those skilled in the art will understand that the claimed subject matter may be practiced without these specific details. In other instances, methods, apparatuses or systems that would be known by one of ordinary skill have not been described in detail so as not to obscure claimed subject matter.

Some portions are presented in terms of algorithms or symbolic representations of operations on data bits or binary digital signals stored within a computing system memory, such as a computer memory. These algorithmic descriptions or representations are examples of techniques used by those of ordinary skill in the data processing arts to convey the substance of their work to others skilled in the art. An algorithm is a self-consistent sequence of operations or similar processing leading to a desired result. In this context, operations or processing involves physical manipulation of physical quantities. Typically, although not necessarily, such quantities may take the form of electrical or magnetic signals capable of being stored, transferred, combined, compared or otherwise manipulated. It has proven convenient at times, principally for reasons of common usage, to refer to such signals as bits, data, values, elements, symbols, characters, terms, numbers, numerals or the like. It should be understood, however, that all of these and similar terms are to be associated with appropriate physical quantities and are merely convenient labels. Unless specifically stated otherwise, it is appreciated that throughout this specification discussions utilizing terms such as "processing," "computing," "calculating," "determining," and "identifying" or the like refer to actions or processes of a computing device, such as one or more computers or a similar electronic computing device or devices, that manipulate or transform data represented as physical electronic or magnetic quantities within memories, registers, or other information storage devices, transmission devices, or display devices of the computing platform.

The system or systems discussed herein are not limited to any particular hardware architecture or configuration. A computing device can include any suitable arrangement of components that provide a result conditioned on one or more inputs. Such computing devices may include, but are not limited to, desktop computers, mobile phones, personal digital assistants (PDAs), tablet computers, laptops, smartphones, Wi-Fi enabled computing devices, 3G or 4G enabled computing devices, or other suitable computing devices. Suitable computing devices include multipurpose microprocessor-based computer systems accessing stored software that programs or configures the computing system from a general purpose computing apparatus to a specialized computing apparatus implementing one or more embodiments of the present subject matter. Any suitable programming, scripting, or other type of language or combinations of languages may be used to implement the teachings contained herein in software to be used in programming or configuring a computing device.

Embodiments of the methods disclosed herein may be performed in the operation of such computing devices. The order of the blocks presented in the examples above can be varied—for example, blocks can be re-ordered, combined, and/or broken into sub-blocks. Certain blocks or processes can be performed in parallel. Thus, while the steps of methods disclosed herein have been shown and described in a particular order, other embodiments may comprise the same, additional, or fewer steps. Some embodiments may perform the steps in a different order or in parallel.

The use of "adapted to" or "configured to" herein is meant as open and inclusive language that does not foreclose devices adapted to or configured to perform additional tasks or steps. Additionally, the use of "based on" is meant to be open and inclusive, in that a process, step, calculation, or other action "based on" one or more recited conditions or values may, in practice, be based on additional conditions or values beyond those recited. Headings, lists, and numbering included herein are for ease of explanation only and are not meant to be limiting.

While the present subject matter has been described in detail with respect to specific embodiments thereof, it will be appreciated that those skilled in the art, upon attaining an understanding of the foregoing may readily produce alterations to, variations of, and equivalents to such embodiments. Accordingly, it should be understood that the present disclosure has been presented for purposes of example rather than limitation, and does not preclude inclusion of such modifications, variations and/or additions to the present subject matter as would be readily apparent to one of ordinary skill in the art.

That which is claimed is:

1. A method, comprising:
   receiving, by a server of a laboratory management organization and from an electronic device of a healthcare provider, a selection of at least one laboratory test from a plurality of selectable laboratory tests specific to the healthcare provider and identifying a patient of the healthcare provider corresponding to the at least one laboratory test:
   determining, by the server of the laboratory management organization, at least one laboratory to complete the at least one laboratory test;
   determining whether enough of a previously-taken sample for the patient is available to be used for testing purposes;
   determining, when enough of the previously-taken sample is available, whether the previously-taken sample has existed too long relative to how long the previously-taken sample can be used for testing purposes;
   determining, by the server of the laboratory management organization, when enough of the previously-taken sample is not available or has existed too long, a specimen collection procedure specific the at least one laboratory to complete the at least one laboratory test when not enough of the previously-taken sample for the patient that has not existed too long is not available; and
   sending, when enough of the previously-taken sample is not available or has existed too long, by the server of the laboratory management organization and to the electronic device of the healthcare provider, the specimen collection procedure prior to collection of a specimen from the patient according to the specimen collection procedure when not enough of the previously-taken sample for the patient that has not existed too long is not available.

2. The method of claim 1, wherein the plurality of selectable laboratory tests specific to the healthcare provider is dynamically determined by the server of the laboratory management organization based on frequently ordered laboratory tests previously ordered by the healthcare provider.

3. The method of claim 1, wherein the plurality of selectable laboratory tests specific to the healthcare provider is dynamically determined by the server of the laboratory management organization based on frequently ordered laboratory tests across a plurality of healthcare providers comprising a same healthcare provider type as the healthcare provider.

4. The method of claim 1, wherein the selection is received using a completed customized electronic laboratory test order form comprising a selection of a disease corresponding to the patient and the plurality of selectable laboratory tests specific to the healthcare provider is dynamically determined by the server of the laboratory management organization based on frequently ordered laboratory tests for the disease.

5. The method of claim 4,
   wherein the completed customized electronic laboratory test order form comprises a required deadline for receiving test results and a required geographic region, and
   wherein, determining by the server of the laboratory management organization, the at least one laboratory to complete the at least one laboratory test further comprises:
   determining at least one available laboratory in the required geographic region capable of completing a first laboratory test and a second laboratory test by the required deadline; and
   selecting a single laboratory from the at least one available laboratory to complete the first laboratory test and second laboratory test.

6. The method of claim 5, wherein selecting, by the server of the laboratory management organization, the single laboratory to complete the first laboratory test and the second laboratory test comprises:
   dynamically determining the single laboratory to complete the first laboratory test and the second laboratory test based on at least two of: a cost of at least one of the first laboratory test or the second laboratory test at the single laboratory, a geographic location of the single laboratory, or a required turnaround time for a test result of at least one of the first laboratory test or the second laboratory test.

7. The method of claim 1, further comprising:
   receiving, by the server of the laboratory management organization and from the at least one laboratory, a laboratory test result for the at least one laboratory test for the patient;
   determining, by the server of the laboratory management organization, a prior historical laboratory test result for at least one laboratory test for the patient;
   generating, by the server of the laboratory management organization, a test results report comprising the laboratory test result for the at least one laboratory test for the patient and the prior historical laboratory test result for at least one laboratory test for the patient; and
   electronically sending, by the server of the laboratory management organization, the test results report to at least one of the healthcare provider or the patient.

8. A non-transitory computer-readable medium comprising one or more software applications configured to be executed by a processor, the one or more software applications configured to cause the processor to:
   receive, from an electronic device of a healthcare provider, a selection of at least one laboratory test from a plurality of selectable laboratory tests specific to the healthcare provider and identifying a patient of the healthcare provider corresponding to the at least one laboratory test:
   determine at least one laboratory to complete the at least one laboratory test;
   determine whether enough of a previously-taken sample for the patient is available to be used for testing purposes;
   determine, when enough of the previously-taken sample is available, whether the previously-taken sample has existed too long relative to how long the previously-taken sample can be used for testing purposes;
   determine when enough of the previously-taken sample is not available or has existed too long, a specimen collection procedure specific the at least one laboratory to complete the at least one laboratory test when not enough of the previously-taken sample for the patient that has not existed too long is not available; and send, when enough of the previously-taken sample is not available or has existed too long, the specimen collection procedure prior to collection of a specimen from the patient according to the specimen collection procedure when not enough of the previously-taken sample for the patient that has not existed too long is not available.

9. The non-transitory computer-readable medium of claim 8, wherein the plurality of selectable laboratory tests specific to the healthcare provider is dynamically determined based on frequently ordered laboratory tests previously ordered by the healthcare provider.

10. The non-transitory computer-readable medium of claim 8, wherein the plurality of selectable laboratory tests specific to the healthcare provider is dynamically determined based on frequently ordered laboratory tests across a plurality of healthcare providers comprising a same healthcare provider type as the healthcare provider.

11. The non-transitory computer-readable medium of claim 8, wherein the selection is received using a completed customized electronic laboratory test order form comprising a selection of a disease corresponding to the patient and the plurality of selectable laboratory tests specific to the healthcare provider is dynamically determined based on frequently ordered laboratory tests for the disease.

12. The non-transitory computer-readable medium of claim 11,
wherein the completed customized electronic laboratory test order form comprises a required deadline for receiving test results and a required geographic region, and
wherein, determining the at least one laboratory to complete the at least one laboratory test further comprises:
determining at least one available laboratory in the required geographic region capable of completing a first laboratory test and a second laboratory test by the required deadline; and
selecting a single laboratory from the at least one available laboratory to complete the first laboratory test and second laboratory test.

13. The non-transitory computer-readable medium of claim 12, wherein selecting the single laboratory to complete the first laboratory test and the second laboratory test comprises:
dynamically determining the single laboratory to complete the first laboratory test and the second laboratory test based on at least two of: a cost of at least one of the first laboratory test or the second laboratory test at the single laboratory, a geographic location of the single laboratory, or a required turnaround time for a test result of at least one of the first laboratory test or the second laboratory test.

14. The non-transitory computer-readable medium of claim 8, wherein the software applications are further configured to cause the processor to:
receive, from the at least one laboratory, a laboratory test result for the at least one laboratory test for the patient;
determine a prior historical laboratory test result for at least one laboratory test for the patient;
generate a test results report comprising the laboratory test result for the at least one laboratory test for the patient and the prior historical laboratory test result for at least one laboratory test for the patient; and
electronically send the test results report to at least one of the healthcare provider or the patient.

15. A system, comprising:
a server corresponding to a laboratory management organization, the server comprising a memory, a network interface, and a processor in communication with the memory and the network interface, the memory comprising executable instructions configured to cause the processor to:
receive, from an electronic device of a healthcare provider, a selection of at least one laboratory test from a plurality of selectable laboratory tests specific to the healthcare provider and identifying a patient of the healthcare provider corresponding to the at least one laboratory test:
determine at least one laboratory to complete the at least one laboratory test;
determine whether enough of a previously-taken sample for the patient is available to be used for testing purposes;
determine, when enough of the previously-taken sample is available, whether the previously-taken sample has existed too long relative to how long the previously-taken sample can be used for testing purposes;
determine when enough of the previously-taken sample is not available or has existed too long, a specimen collection procedure specific the at least one laboratory to complete the at least one laboratory test when not enough of the previously-taken sample for the patient that has not existed too long is not available; and
send, when enough of the previously-taken sample is not available or has existed too long, the specimen collection procedure prior to collection of a specimen from the patient according to the specimen collection procedure when not enough of the previously-taken sample for the patient that has not existed too long is not available.

16. The system of claim 15, wherein the plurality of selectable laboratory tests specific to the healthcare provider is dynamically determined based on frequently ordered laboratory tests previously ordered by the healthcare provider.

17. The system of claim 15, wherein the plurality of selectable laboratory tests specific to the healthcare provider is dynamically determined based on frequently ordered laboratory tests across a plurality of healthcare providers comprising a same healthcare provider type as the healthcare provider.

18. The system of claim 15 further comprising the electronic device of the healthcare provider, and wherein the selection is made using a completed customized electronic laboratory test order form displayed on the electronic device of the healthcare provider to include a selection of a disease corresponding to the patient, and the plurality of selectable laboratory tests specific to the healthcare provider is dynamically determined based on frequently ordered laboratory tests for the disease;
wherein the completed customized electronic laboratory test order form comprises a required deadline for receiving test results and a required geographic region, and
wherein, determining the at least one laboratory to complete the at least one laboratory test further comprises:
determining at least one available laboratory in the required geographic region capable of completing a first laboratory test and a second laboratory test by the required deadline; and selecting a single laboratory from the at least one available laboratory to complete the first laboratory test and second laboratory test.

19. The system of claim 18, wherein selecting the single laboratory to complete the first laboratory test and the second laboratory test comprises:
dynamically determining the single laboratory to complete the first laboratory test and the second laboratory test based on at least two of: a cost of at least one of the first laboratory test or the second laboratory test at the single laboratory, a geographic location of the single laboratory, or a required turnaround time for a test result of at least one of the first laboratory test or the second laboratory test.

20. The system of claim 15, wherein the executable instructions are further configured to cause the processor to:
receive, from the at least one laboratory, a laboratory test result for the at least one laboratory test for the patient;
determine a prior historical laboratory test result for at least one laboratory test for the patient;
generate a test results report comprising the laboratory test result for the at least one laboratory test for the patient and the prior historical laboratory test result for at least one laboratory test for the patient; and
electronically send the test results report to at least one of the healthcare provider or the patient.

\* \* \* \* \*